United States Patent [19]

Lee et al.

[11] Patent Number: 5,686,458
[45] Date of Patent: Nov. 11, 1997

[54] QUINAZOLINE DERIVIATES FOR TREATING PEPTIC ULCER

[75] Inventors: Jong Wook Lee, Kwacheon; Jeong Seok Chae, Seoul; Chang Seop Kim, Suwon; Jae Kyu Kim, Suwon; Dae Sung Lim, Kuro; Jeong Won Lee, Anyang; Moon Kyu Shon, Anyang; Dae Woong Jo, Anyang, all of Rep. of Korea

[73] Assignee: Yuhan Corporation, Seoul, Rep. of Korea

[21] Appl. No.: 464,796

[22] PCT Filed: Oct. 29, 1993

[86] PCT No.: PCT/KR93/00096

§ 371 Date: Jun. 26, 1995

§ 102(e) Date: Jun. 26, 1995

[87] PCT Pub. No.: WO94/14795

PCT Pub. Date: Jul. 7, 1994

[30] Foreign Application Priority Data

Dec. 29, 1992 [KR] Rep. of Korea ............ 92-26290

[51] Int. Cl.$^6$ ............ A61K 31/505; C07D 403/02
[52] U.S. Cl. ............ 514/260; 544/284
[58] Field of Search ............ 544/284, 291; 514/260

[56] References Cited

U.S. PATENT DOCUMENTS

| | | | |
|---|---|---|---|
| 3,956,495 | 5/1976 | Lacefield | 424/251 |
| 3,960,861 | 6/1976 | Danilewicz et al. | 260/256.4 |
| 4,044,136 | 8/1977 | Danilewicz et al. | 424/251 |
| 5,064,833 | 11/1991 | Ife et al. | 514/260 |
| 5,444,062 | 8/1995 | Coe et al. | 514/260 |

FOREIGN PATENT DOCUMENTS

| | | |
|---|---|---|
| 0322133 | 12/1988 | European Pat. Off. . |
| 0404322 | 5/1990 | European Pat. Off. . |
| 92/07844 | 5/1992 | WIPO . |

*Primary Examiner*—Matthew V. Grumbling
*Attorney, Agent, or Firm*—Anderson Kill & Olick, PC

[57] ABSTRACT

A quinazoline derivative represented by formula(I) or a pharmaceutically acceptable salt thereof is useful for the treatment of peptic ulcer, wherein:

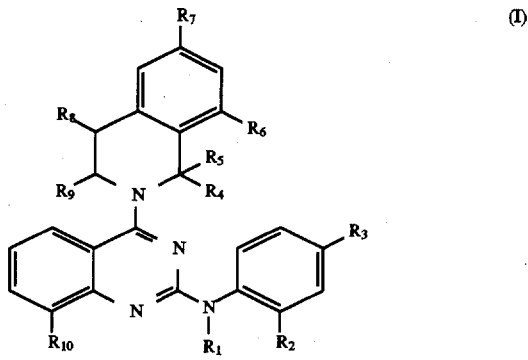

$R_1$ and $R_2$ are each hydrogen or a $C_1$–$C_4$ alkyl group;
$R_3$ is hydrogen or a halogen;
$R_4$, $R_5$, $R_6$, $R_7$, $R_8$ and $R_9$, which may be the same or different, are each hydrogen, a $C_1$–$C_4$ alkyl group, a cyclopropyl group, or a $C_1$–$C_4$ alkyl group substituted with a halogen; and
$R_{10}$ is a methoxy group.

9 Claims, 3 Drawing Sheets

QUINAZOLINE DERIVIATES FOR TREATING PEPTIC ULCER

This is a 371 of PCT/KR93/00096 filed Oct. 29, 1993.

FIELD OF THE INVENTION

The present invention relates to novel quinazoline derivatives and pharmaceutically acceptable salts thereof which possess an excellent anti-secretory activity, pharmaceutical compositions containing the same as an active ingredient, their novel intermediates, and processes for the preparation thereof.

BACKGROUND OF THE INVENTION

For the treatment of peptic ulcer disease, various drugs such as antacid, anticholinergic agent and $H_2$-receptor antagonist have been used. Recently, the advent of omeprazole useful as a proton pump inhibitor has rekindled research activities in this field.

However, it has been pointed out that the proton pump inhibition by omeprazole is irreversible, which may induce side effects. Accordingly, various attempts to develop a reversible proton pump inhibitor are being actively made. For example, European Patent Nos. 322133 and 404322 disclose quinazoline derivatives involving a reversible proton pump inhibitor.

SUMMARY OF THE INVENTION

The present inventors have carried out extensive research to develop a reversible proton pump inhibitor with improved efficacy; and, as a result, have discovered that quinazoline derivatives having a tetrahydroisoquinoline group at the 4-position of the quinazoline nucleus exhibit excellent proton pump inhibition effects and have the ability to attain a reversible proton pump inhibition.

Accordingly, it is an object of the present invention to provide novel quinazoline derivatives having a tetrahydroisoquinoline group at the 4-position of the quinazoline nucleus, and pharmaceutically acceptable salts thereof.

It is another object of the present invention to provide processes for preparing said compounds.

It is a further object of the present invention to provide pharmaceutical compositions containing the same as active ingredients.

It is still another object of the invention to provide novel intermediate compounds useful for the preparation of the inventive quinazoline derivatives.

BRIEF DESCRIPTION OF THE DRAWINGS

The present invention may be more fully understood with reference to the following drawings, wherein.

DETAILED DESCRIPTION OF THE INVENTION

Figure 1:
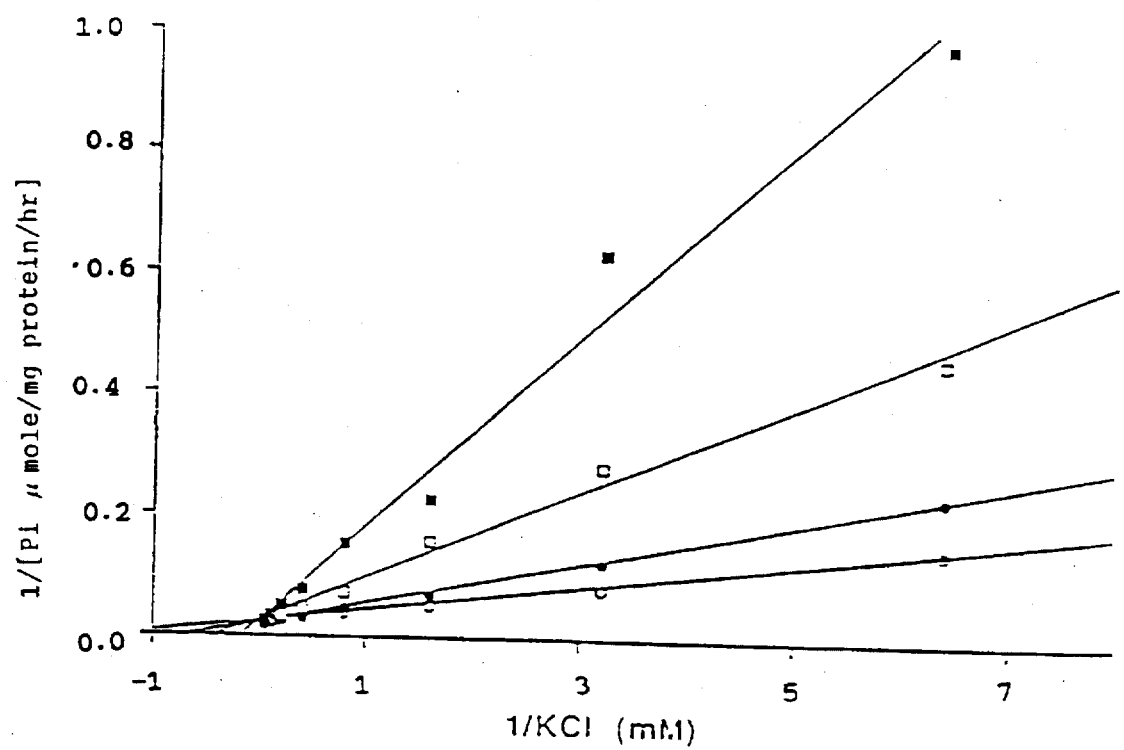
FIGS. 1 to 3 depict the Lineweaver-Burk plots of the specific activities obtained from an exemplary inventive compound, omeprazole and SK&F96067.

In accordance with the present invention, there is provided novel quinazoline derivatives of formula(I) and their pharmaceutically acceptable salts:

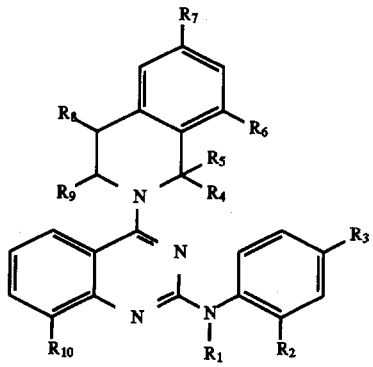

wherein, $R_1$ and $R_2$ are each hydrogen or a $C_1$–$C_4$ alkyl group;

$R_3$ is hydrogen or a halogen;

$R_4$, $R_5$, $R_6$, $R_7$, $R_8$ and $R_9$, which may be the same or different, are each hydrogen, a $C_1$–$C_4$ alkyl group, a cyclopropyl group, or a $C_1$–$C_4$ alkyl group substituted with a halogen;

and $R_{10}$ is a methoxy group.

Among the compounds of the present invention, preferred are those wherein;

$R^1$ and $R_2$ are $C_1$–$C_4$ alkyl group;

$R_3$ is halogen;

$R_4$, $R_5$, $R_6$, $R_7$, $R_8$ and $R_9$, which may be the same or different, hydrogen, a $C_1$–$C_4$ alkyl group or a $C_1$–$C_4$ alkyl group substituted with a halogen.

$R_{10}$ is $C_1$–$C_4$ alkoxy.

Particularly, preferred compounds of the present invention are listed below:

2-(phenylamino)-4-(1,2,3,4-tetrahydroisoquinoline-2-yl) quinazoline;

2-(N-phenylmethylamino)-4-(1,2,3,4-tetrahydroisoquinoline-2-yl)quinazoline;

2-(4-fluoro-N-methyl-phenylamino)-4-(1,2,3,4-tetrahydroisoquinoline-2-yl)quinazoline;

2-(2-methylphenylamino)-4-(1,2,3,4-tetrahydroisoquinoline-2-yl)quinazoline;

2-(4-fluoro-2-methyl-phenylamino)-4-(1,2,3,4-tetrahydroisoquinoline-2-yl)quinazoline;

2-(4-fluorophenylamino)-4-(1,2,3,4-tetrahydroisoquinoline-2-yl)quinazoline;

2-(N-methylphenylamino)-4-(1-methyl-1,2,3,4-tetrahydroisoquinoline-2-yl)quinazoline;

2-(4-fluorophenylamino)-4-(1-methyl-1,2,3,4-tetrahydroisoquinoline-2-yl)quinazoline;

2-(4-fluoro-2-methyl-phenylamino)-4-(1-methyl-1,2,3,4-tetrahydroisoquinoline-2-yl)quinazoline;

2-(4-fluoro-2-methyl-phenylamino)-4-(1,8-ethano-1,2,3,4-tetrahydroisoquinoline-2-yl)quinazoline;

8-methoxy-2-(phenylamino)-4-(1,2,3,4-tetrahydroisoquinoline-2-yl)quinazoline;

8-methoxy-(N-methylphenylamino)-4-(1,2,3,4-tetrahydroisoquinoline-2-yl)quinazoline;

8-methoxy-2-(4-fluorophenylamino)-4-(1,2,3,4-tetrahydroisoquinoline-2-yl)quinazoline;

8-methoxy-2-(4-fluoro-2-methyl-phenylamino)-4-(1,2,3,4-tetrahydroisoquinoline-2-yl)quinazoline;

8-methoxy-2-(4-fluoro-N-methyl-phenylamino)-4-(1,2,3,4-tetrahydroisoquinoline-2-yl)quinazoline;

8-methoxy-2-(4-fluorophenylamino)-4-(1-methyl-1,2,3,4-tetrahydroisoquinoline-2-yl)quinazoline;

8-methoxy-2-(4-fluoro-2-methyl-phenylamino)-4-(1-methyl-1,2,3,4-tetrahydroisoquinoline-2-yl)quinazoline;

(R)-8-methoxy-2-(4-fluoro-2-methyl-phenylamino)-4-(1-methyl-1,2,3,4-tetrahydroisoquinoline-2-yl)quinazoline;

(S)-8-methoxy-2-(4-fluoro-2-methyl-phenylamino)-4-(1-methyl-1,2,3,4-tetrahydroisoquinoline-2-yl)quinazoline;

8-(2-hydroxyethyloxy)-2-(4-fluoro-2-methyl-phenylamino)-4-(1-methyl-1,2,3,4-tetrahydroisoquinoline-2-yl)quinazoline;

2-(4-fluoro-2-methylphenylamino)-8-ethoxy-4-(1-methyl-1,2,3,4-tetrahydroisoquinoline-2-yl)quinazoline;

2-(4-fluoro-2-methylphenylamino)-8-(methylthiomethyloxy)-4-(1-methyl-1,2,3,4-tetrahydroisoquinoline-2-yl) quinazoline;

8-methoxy-2-(N-methylphenylamino)-4-(1-methyl-1,2,3,4-tetrahydroisoquinoline-2-yl)quinazoline;

8-methoxy-2-(4-fluoro-N-methylphenylamino)-4-(1-methyl-1,2,3,4-tetrahydroisoquinoline-2-yl)quinazoline;

2-(4-fluoro-2-methylphenylamino)-8-methoxy-4-(1,2,3,4-tetrahydroisoquinoline-2-yl)quinazoline;

2-(4-fluorophenylamino)-8-methoxy-4-(1-fluoromethyl-1,2,3,4-tetrahydroisoquinoline-2-yl)quinazoline;

2-(4-fluoro-2-methylphenylamino)-8-methoxy-4-(1-fluoromethyl-1,2,3,4-tetrahydroisoquinoline-2-yl)quinazoline;

8-methoxy-2-(4-fluorophenylamino)-4-(1-ethyl-1,2,3,4-tetrahydroisoquinoline-2-yl)quinazoline;

8-methoxy-2-(2-methyl-4-fluorophenylamino)-4-(1-ethyl-1,2,3,4-tetrahydroisoquinoline-2-yl)quinazoline;

2-(4-fluoro-2-methylphenylamino)-8-methoxy-4-(1-cyclopropyl-1,2,3,4-tetrahydroisoquinoline-2-yl)quinazoline;

2-(4-fluorophenylamino)-8-methoxy-4-(3-methyl-1,2,3,4-tetrahydroisoquinoline-2-yl)quinazoline;

2-(4-fluoro-2-methylphenylamino)-8-methoxy-4-(3-methyl-1,2,3,4-tetrahydroisoquinoline-2-yl)quinazoline;

2-(4-fluorophenylamino)-8-methoxy-4-(1,1-dimethyl-1,2,3,4-tetrahydroisoquinoline-2-yl)quinazoline;

2-(4-fluoro-2-methylphenylamino)-8-methoxy-4-(1,1-dimethyl-1,2,3,4-tetrahydroisoquinoline-2-yl)quinazoline;

2-(4-fluorophenylamino)-8-methoxy-4-(1,1-dimethyl-1,2,3,4-tetrahydroisoquinoline-2-yl)quinazoline;

2-(4-fluoro-2-methylphenylamino)-8-methoxy-4-(1,8-dimethyl-1,2,3,4-tetrahydroisoquinoline-2-yl)quinazoline;

2-(4-fluorophenylamino)-8-methoxy-4-(1,6-dimethyl-1,2,3,4-tetrahydroisoquinoline-2-yl)quinazoline;

2-(4-fluoro-2-methylphenylamino)-8-methoxy-4-(1,6-dimethyl-1,2,3,4-tetrahydroisoquinoline-2-yl)quinazoline;

2-(4-fluorophenylamino)-8-methoxy-4-(1,4-dimethyl-1,2,3,4-tetrahydroisoquinoline-2-yl)quinazoline;

2-(4-fluoro-2-methylphenylamino)-8-methoxy-4-(1,4-dimethyl-1,2,3,4-tetrahydroisoquinoline-2-yl)quinazoline;

8-methoxy-2-(4-fluorophenylamino)-4-(1,8-ethano-1,2,3,4-tetrahydroisoquinoline-2-yl)quinazoline;

8-methoxy-2-(4-fluoro-2-methylphenylamino)-4-(1,8-ethano-1,2,3,4-tetrahydroisoquinoline-2-yl)quinazoline; and 2-(4-fluoro-2-methylphenylamino)-8-methoxy-4-(1-methyl-1,2,3,4-tetrahydroisoquinoline-2-yl)quinazoline.

The quinazoline derivatives of formula(I) in the present invention may exist in the form of an optical isomer, (R) or (S), or a mixture thereof. Both types of the isomeric compounds are found to exhibit excellent anti-secretory activity.

The compound of formula(I) may be prepared by a process which comprises reacting a compound of formula (II) with a compound of formula(III) to give a compound of formula(IV), which is then reacted with a compound of formula(V), as follows:

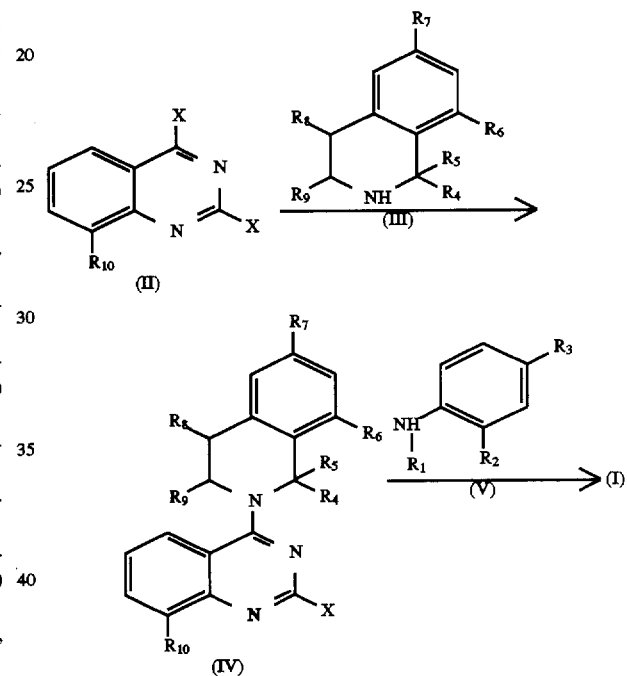

wherein, $R_1$ and $R_2$ are each hydrogen or a $C_1$–$C_4$ alkyl group;

$R_3$ is hydrogen or a halogen;

$R_4$, $R_5$, $R_6$, $R_7$, $R_8$ and $R_9$, which may be the same or different, are each hydrogen, a $C_1$–$C_4$ alkyl group, a cyclopropyl group, or a $C_1$–$C_4$ alkyl group substituted with a halogen;

$R_{10}$ is a methoxy group.

The compounds of formula(II) may be prepared in accordance with a known method, e.g., the one disclosed in European Patent No. 0322133. Further, the compounds of formula(V) are commercially available(for example Aldrich Co. in U.S.A.)

The compounds of formula(II) are reacted with the compounds of formula(III) in an appropriate solvent and a base for 1 to 24 hours to give the compounds of formula (IV). Suitable solvents for this reaction may include dichloromethane, acetone, acetonitrile, dimethylformamide tetrahydrofuran and a mixture thereof with water. The reaction temperature is preferably between a room temperature and 150° C. Suitable bases for this reaction may include triethylamine, N,N-dimethylaniline and pyridine.

The compounds of formula(IV) thus obtained are then reacted with the compounds of formula(V) in an appropriate solvent for 2 to 4 hours to give the present compounds of formula(I). Suitable solvents for this reaction may include dimethylformamide, p-dioxane, dimethylsulfoxide and the like. The reaction temperature is preferably between 80° and 120° C.

The compounds of formula(IV) prepared as above are novel and useful as an intermediate for the preparation of the quinazoline compounds of formula(I). Therefore, the present invention encompasses, within its scope, the novel compounds of formula(IV) and processes for the preparation thereof.

The compounds of the present invention may be administered, either orally or intraperitoneally, in an effective amount ranging from 0.1 mg/kg to 500 mg/kg, preferably from 1.0 mg/kg to 100 mg/kg into a subject patient per day.

The present invention further includes, within its scope, pharmaceutically acceptable salts of the compounds of formula(I). The non-toxic salts which fall within the scope of the present invention may include inorganic acid salts such as hydrochloride, sulfate, phosphate and nitrate, and organic acid salts such as tartrate, fumarate, citrate, mesylate and acetate.

The pharmaceutically acceptable salts may be prepared in accordance with a known method, e.g., by reacting the compounds of formula(I) with the acids mentioned above in the presence of a solvent, e.g., methane, ethane, dichloromethane, ethyl acetate and diethyl ether.

The present invention also includes within its scope pharmaceutical compositions comprising one or more of the inventive compounds as a active ingredient, in association with a pharmaceutically acceptable carrier, excipient and/or other additives, if necessary. The active ingredient present in the composition may range from 0.1% to 99.9% by weight thereof.

The following Examples are given for the purpose of illustration only, and are not intended to limit the scope of the invention.

PREPARATION 1

Preparation of Substituted 1,2,3,4-Tetrahydroisoquinoline of Formula(III)

Preparation 1-1: 1-Methyl-1,2,3,4-Tetrahydroisoquinoline

Step 1: Preparation of N-(2-Phenylethyl)Acetamide 12.6 ml of phenethylamine(0.1M) and 14 ml of triethylamine(0.1M) were dissolved in 100 ml of dichloromethane; and 6.9 ml of acetyl chloride(0.1M) was dropwise added thereto while maintaining the temperature of the reaction system below 0° C., followed by stirring at a room temperature for 10 minutes. The reaction solution was washed with water, dried over anhydrous magnesium sulfate and concentrated under a reduced pressure to give 14.23 g Of the title compound as white solids.

Step 2: Preparation of 1-Methyl-3,4-Dihydroisoquinoline 8.43 g of the compound(51.6 mM) prepared in Step 1 above was added to 84.36 g of polyphosporic acid, which was reacted at 160° C. for 1.5 hours with stirring. The reaction solution was poured into ice water, neutralized with ammonia water, and extracted from ethyl acetate. The extract was dried over anhydrous magnesium sulfate and concentrated under a reduced pressure. The residue thus obtained was subjected to silica gel column chromatography using a mixed solvent of methanol:dichloromethane (1:20 (v/v)) as a developing solvent to give 6.48 g of the title compound as oily substance.

Step 3: Preparation of 1-Methyl-1,2,3,4-Tetrahydroisoquinoline 1.76g of sodium borohydride(46 mM) was suspended in 80 ml of ethanol, and 6.48 g of the compound(44.6 mM) prepared in Step 2 above was added thereto. The resultant mixture was stirred at an ambient temperature for an hour and cooled to below 5° C., which was then acidified by adding dilute hydrochloric acid. After making the reaction solution alkaline by adding sodium hydroxide, it was extracted from ethyl acetate. The ethyl acetate layer was dried over anhydrous sodium sulfate and concentrated under a reduced pressure to give 6.17 g of the title compound as oily substance.

Preparation 1-2: (R)-1-Methyl-1,2,3,4-Tetrahydroisoquinoline

Step 1: Preparation of (R)-1-Methyl-4-Methylthio-1,2,3,4-Tetrahydroisoquinoline-3-One 27.85 ml of (R)-1-phenylethylamime(0.21M) and 30 ml of triethylamine(0.21M) were dissolved in 200 ml of dichloromethane and cooled to 0° C. 37.8 g of α-chloro-α-(methylthio)-acetyl chloride(0.21M) was dropwise added thereto at 0° C. The resultant was stirred at room temperature for 30 minutes, added with tin(IV) chloride and, further stirred for 30 minutes at room temperature.

The reaction solution was poured into ice water and washed with water. The organic layer was dehydrated and concentrated to give 32.5 g of the title compound in solid form.

Step 2: Preparation of (R)-1-Methyl-1,2,3,4-Tetrahydroisoquinoline-3-One 150 g of Raney nickel was suspended in 300 ml of ethanol and 32.5 g of the compound(0.16M) prepared in Step 1 above was added thereto. After stirring the mixture at room temperature for 3 days, the Raney nickel was removed by the filtration, and the filtrate was concentrated to give 20 g of the title compound in solid form.

Step 3: Preparation of (R)-1-Methyl-1,2,3,4-Tetrahydroisoquinoline 10.0 g of the compound(62 mM) prepared by Step 2 above and 20 ml of tetrahydrofuran were mixed, and 9 ml of 10.2M borane-methylsulfide complex was dropwise added thereto. The mixture was reacted under reflux for an hour and cooled to room temperature. By adding 10 ml of 6N HCl to the reaction solution, the remaining borane-methylsulfide complex was destroyed and the resultant was neutralized with 10% NaOH. The reaction solution was extracted from ethyl acetate, dehydrated and concentrated to give 8.8 g of the title compound in oil form.

Preparation 1-3: (S)-1-Methyl-1,2,3,4-Tetrahydroisoquinoline

In accordance with the same procedures as in Preparation 1-2, except that 25.6 ml of (S)-1-phenylethyl-amine( 0.20M) and 34.8 g of α-chloro-α-(methylthio)-acetyl chloride (0.22M) were used as starting materials, 8.8 g of the title compound was obtained in oil form.

Preparation 1-4: 1,8-Ethano-1,2,3,4-Tetrahydroisoquinoline

Step 1: Preparation of 3,4-Dihydroisoquinoline 18.8 ml of 1,2,3,4-tetrahydroisoquinoline(0.15M) was dissolved in 400 ml of dichloromethane; and 29.4 g of N-bromosuccinimide(0.165M) was slowly added thereto at room temperature followed by stirring for 30 minutes. To this, 100 ml of aqueous sodium hydroxide(30%) was added and further stirred for an hour. The organic layer was separated, washed with water and extracted from aqueous hydrochloric acid solution. Ammonia water was added to adjust the pH to 9; and extracted from dichloromethane, washed with water, dried over anhydrous sodium sulfate and concentrated to give 18.5 g of the title compound in oil form.

Step 2: Preparation of 1,2,3,4-Tetrahydroisoquinoline-1-Acetic Acid

A mixture containing 18.5 g of the compound(0.14M) prepared in Step 1 above and 14.5 g of malonic acid(0.14M) was stirred at 120° C. for an hour and cooled to room temperature. Thereto, a mixture solution of methanol and water(4:1) was added, stirred and filtered to give 11.2 g of the title compound.

Step 3: Preparation of N-(Methoxycarbonyl)-1,2,3,8a-Tetra-Hydroxychloropent Isoquinoline-7(8H)-One 11.16 g of phosphorous pentoxide was dissolved in 75.35 ml of methane sulfonic acid and heated to 150° C.; and 11.16 g of the compound(58.3 mM) prepared in Step 2 was added thereto. The reaction solution was stirred at 150° C. for 30 minutes and, then cooled to room temperature, which was added with 1.5l of 1N sodium hydroxide and extracted from dichloromethane. The extract thus obtained was dried over potassium carbonate and 8.94 ml of methyl chloro-formate was added thereto, which was stirred for an hour, concentrated and purified by silica gel column chromatography to give 7.2 g of the title compound.

Step 4: Preparation of N-(Methoxycarbonyl)-1,8-Ethano-1,2,3,4-Tetrahydroisoquinoline 7.2 g of the compound(31.3 mM) prepared in Step 3 above was dissolved in 100 ml of acetic acid and subjected to hydrogenation by using 1 g of 10% palladium/active carbon as a catalyst. The palladium/active carbon was filtered out and the filtrate was concentrated under a reduced pressure. The residue was purified by silica gel column chromatography to give 5.7 g of the title compound.

Step 5: Preparation of 1,8-Ethano-1,2,3,4-Tetrahydroisoquinoline

A mixture containing 5.7 g of the compound prepared in Step 4, 340 ml of aqueous potassium hydroxide(10%) and 340 ml of ethylene glycol was heated at 100° C. for 14 hours, cooled to room temperature and extracted from ethyl ether. The extract was washed with water, dried over magnesium sulfate and concentrated under a reduced pressure to give 3.7 g of the title compound.

Preparation 1-5: 1-Trifluoromethyl-1,2,3,4-Tetrahydroisoquinoline

In accordance with the same procedures as in Preparation 1-1, except that 25 ml of phenethylamine(0.2M) and 30 ml of anhydrous trifluoroacetic acid(0.21M) were used as starting materials, 5.4 g of the title compound was prepared.

Preparation 1-6: 1-Fluoromethyl-1,2,3,4-Tetrahydroisoquinoline

Step 1: Preparation of N-(2-Phenylethyl)Fluoroacetamide

To a mixture containing 11.7 g of fluoroacetic acid (0.15M), 27.3 ml of dicyclohexylcarbodiimide(0.17M) and 200 ml of dichloromethane was dropwise added 17 ml of phenethylamine(0.17M), which was stirred for 12 hours. The solids produced were filtered and the filtrate was washed with water, dried over anhydrous sodium sulfate and concentrated. The residue was purified by silica gel column chromatography to give 11.9 g of the title compound as white solids.

Step 2: Preparation of 1-Fluoromethyl-3,4-Dihydroiso-Quinoline

In accordance with the same procedures as in Step 2 of Preparation 1-1, except that 11.9 g of the compound (65 mM) prepared in Step 1 above was used as a starting material, 7.7 g of the title compound was prepared.

Step 3: Preparation of 1-fluoromethyl-1,2,3,4-Tetrahydroisoquinoline

In accordance with the same procedures as in Step 3 of Preparation 1-1, except that 7.6 g of the compound(46 mM) prepared in Step 2 above was used as a starting material, 7.0 g of the title compound was prepared.

Preparation 1-7: 1-Ethyl-1,2,3,4-Tetrahydroisoquinoline

In accordance with the same procedures as in Preparation 1-1, except that 11.3 ml of phenethylamine (90 mM) and 7.8 ml of propionyl chloride(90 mM) were used as starting materials, 8.48 g of the title compound was prepared.

Preparation 1-8: 1-Cyclopropyl-1,2,3,4-Tetrahydroisoquinoline

In accordance with the same procedures as in Preparation 1-1, except that 12.5 ml of phenethylamine (0.1M) and 10 ml of cyclopropane carbonylchloride(0.11M) were used as starting materials, 2.5 g of the title compound was prepared.

Preparation 1-9: 3-Methyl-1,2,3,4-Tetrahydroisoquinoline 3.0 g of 3-methylisoquinoline(21 mM) and 50 ml of methanol were mixed and 0.84 g of platinum oxide was added thereto. The mixture was subjected to hydrogenation at 40 psi and filtered. The filtrate was concentrated under a reduced pressure, to give 3.3 g of the title compound.

Preparation 1-10: 1,1-Dimethyl-1,2,3,4-Tetrahydroisoquinoline

Step 1: Preparation of 1-Methyl-N-Phenylmethyl-3,4-Dihydroisoquinoline Bromide

A mixture containing 20 g of the compound(0.14M) prepared in Step 2 of Preparation 1-1, 18 ml of benzyl bromide(0.15M) and 150 ml of acetonitrile was heated under reflux for 12 hours and cooled to room temperature. The solids produced were filtered and dried to give 22 g of the title compound.

Step 2: Preparation of 1,1-Dimethyl-N-Phenylmethyl-1,2,3,4-Dihydroisoquinoline 20g of the compound(0.06M) prepared in Step 1 above and 80 ml of anhydrous ethyl ether were mixed, and 60 ml of methyl magnesium bromide(3.0M ethyl ether solution) was dropwise added thereto. The mixture was heated for 6 hours under reflux, cooled to room temperature and then stirred for 12 hours. An aqueous ammonium chloride solution was added to the reaction solution and the organic layer was separated, dried over anhydrous sodium sulfate and concentrated under a reduced pressure. The residue produced was purified by silica gel column chromatography to give 11.4 g of the title compound.

Step 3: Preparation of 1,1-Dimethyl-1,2,3,4-Tetrahydroisoquinoline 11 g of the compound(44 mM) prepared in Step 2 above and 80 ml of acetic acid were mixed and 10% palladium/ charcoal was added thereto, which was subjected to hydrogenation at 40 psi and filtered. The filtrate was concentrated under a reduced pressure and basified with aqueous NaOH solution. After extracting the resultant with dichloromethane, the extract was dried over anhydrous sodium sulfate and concentrated, to give 6.78 g of the title compound.

Preparation 1-11: 1,8-Dimethyl-1,2,3,4-Tetrahydroisoquinoline

Step 1: Preparation of 1-(2'-Methylphenyl)Ethylamine 26 ml of 2-methylacetophenone(0.2M), 32 ml of formamide and 7.5 ml of formic acid were mixed and reacted at 160° C. for 5 hours while distilling water off. The resultant was cooled to room temperature and extracted from ethyl ether. The extract was washed with water, concentrated under a reduced pressure, added with 20 ml of concentrated hydrochloric acid and heated under reflux for an hour. The reaction solution was cooled to room temperature, washed with ethyl ether and neutralized with aqueous NaOH solution. After extracting the resultant with ethyl ether, the extract was dried over anhydrous sodium sulfate and concentrated under a reduced pressure, to give 16.9 g of the title compound.

Step 2: Preparation of N-(Ethoxycarbonylmethyl)-1-(2'-Methylphenyl)Ethylamine 16.8 g of the compound(0.124M) prepared in Step 1 above, 17.3 ml of triethylamine and 100 ml of tetrahydrofuran were mixed and 13.8 ml of ethyl bromoacetate (0.124M) was dropwise added thereto, followed by heating under reflux for an hour. The resultant was stirred at room temperature for 12 hours and added with ethyl ether. After filtering the solids produced, the filtrate was washed with water, dried over anhydrous sodium sulfate and concentrated under a reduced pressure. The residue was purified by silica gel column chromatography, to give 23.3 g of the title compound.

Step 3: Preparation of N-(2-Hydroxyethyl)-1-(2-Methyl-Phenyl)Ethylamine

To a mixture of 3.8 g of lithium aluminium hydride (0.1M) and 150 ml of tetrahydrofuran, 23.3 g of the compound (0.105M) prepared in Step 2 above was dropwise added at room temperature and stirred for 30 minutes. The resultant was added with water and solids produced were filtered. The filtrate was dried over anhydrous sodium sulfate and concentrated under a reduced pressure, to give 13.8 g of the title compound.

Step 4: Preparation of N-(2-Bromoethyl)-1-(2'-Methyl-Phenyl)Ethylamine Hydrochloride 77 ml of 48% HBr was cooled to 0° C. and dropwise added at 0° C. to 13.8 g of the compound(77 mM) prepared in Step 3 above. Then, 50 ml of the reaction solution was distilled off and the residue was cooled to room temperature. The solids obtained were recrystallized in a mixed solvent of ethanol and ethyl ether to produce 14.75 g of the title compound.

Step 5: Preparation of 1,8-Dimethyl-1,2,3,4-Tetrahydroisoquinoline

To a mixed solution of 14.7 g of the compound (45.5 mM) prepared in Step 4 above and 100 ml of decaline, was added aluminium chloride and reacted at 140°–150° C. for 1.5 hours, which was cooled to 0° C. The reaction mixture was diluted by pouring into ice water and washed with ethyl ether. The reaction mixture was basified by adding aqueous NaOH solution and the solids produced were filtered. The filtrate was extracted from ethyl ether and the extracts was dried over anhydrous sodium sulfate, concentrated under a reduced pressure, to give 3.16 g of the title compound.

Preparation 1-12: 1,6-Dimethyl-1,2,3,4-Tetrahydroisoquinoline

In accordance with the same procedures as in Preparation 1-11, except that 13.41 g of 4-methylaceto-phenone(0.2M) was used as a starting material, 2.8 g of the title compound was prepared.

Preparation 1-13: 1,4-Dimethyl-1,2,3,4-Tetrahydroisoquinoline

In accordance with the same procedures as in Preparation 1-1, except that 14.5 ml of β-methylphenethyl-amine(0.1M) and 7.8 ml of acetyl chloride(0.11M) were used as starting materials, 6.6 g of the title compound was prepared.

Preparation 2: Preparation of Substituted 2,4-Dichloro-Quinazolines of Formula(II):

Preparation 2-1: 2,4-Dichloroquinazoline

Step 1: Preparation of 2,4-Dihydroxyquinazoline

To a mixture containing 41 g of 2-aminobenzoic acid (0.3M), 21 of water and 34 ml of acetic acid, was dropwise added 54 g of potassium cyanate dissolved in 200 ml of water. The resultant was stirred for an hour and slowly added with 60 g of 0.3M aqueous sodium hydroxide so as not to exceed the reaction temperature of 40° C. The solution, while heated to 90° C., was stirred for 30 minutes, and then cooled to 0° C. The resultant was acidified by adding a concentrated hydrochloric acid and the solids thus produced were filtered to obtain 43.7 g of the title compound.

Step 2: Preparation of 2,4-Dichloroquinazoline

To 81 g of the compound(0.5M) prepared in Step 1 above, 200 ml of phosphorous oxychloride and 28 ml of dimethylaniline were added; and the resultant was heated under reflux for 5 hours. The reaction mixture was concentrated under a reduced pressure, to give 40.2 g of the title compound as pale yellow solids.

Preparation 2-2: 8-Methoxy-2,4-Dichloroquinazoline

In accordance with the same procedures as in Preparation 2-1, except that 57 g of 2-amino-3-methoxy-benzoic acid (0.43M) was used as a starting material 36 g of the title compound was obtained.

2-Chloro-4-(substituted-1,2,3,4-tetrahydroisoquinoline-2-yl)quinazolines of formula(IV) are prepared in Examples 1-17

Example 1: Preparation of 2-Chloro-4-(1,2,3,4-Tetrahydroisoquinoline-2-Yl) Quinazoline 10 g Of the compound(50.2 mM) prepared in Preparation 2-1, 70 ml of dichloromethane and 7.8 ml of triethylamine (56 mM) were mixed and 6.4 ml of 1,2,3,4-tetrahydroisoquinoline(50.2 mM) was dropwise added slowly while maintaining the reaction temperature below 10° C., which was stirred at room temperature for 2 hours. The reaction mixture was dried over anhydrous sodium sulfate and concentrated under a reduced pressure. The residue was crystallized to give 14.6 g of the title compound.

Example 2: Preparation of 2-Chloro-4-(1-Methyl-1,2,3,4-Tetrahydroisoquinoline-2-Yl)Quinazoline In accordance with the same procedures as in Example 1, except that 10 g of the compound(50.2 mM) prepared in Preparation 2-1 and 7.4 ml of the compound(50.2 mM) prepared in Preparation 1-1 were used as starting materials, 13.5 g of the title compound was prepared.

Example 3: Preparation of 2-Chloro-4-(1,8-Ethano-1,2,3,4-Tetrahydroisoquinoline-2-Yl)Quinazoline In accordance with the same procedures as in Example 1, except that 2.31 g of the compound(11.6 mM) prepared in Preparation 2-1 and 1.85 g of the compound(11.6 mM) prepared in Preparation 1-4 were used as starting materials, 3.0 g of the title compound was prepared.

Example 4: Preparation of 2-Chloro-8-Methoxy-4-(1,2,3,4-Tetrahydroisoquinoline-2-Yl)Quinazoline In accordance with the same procedures as in Example 1, except that 11.2 g of the compound(48.8 mM) prepared in Preparation 2-2 and 6.2 ml of 1,2,3,4-tetrahydroisoquinoline (48.8 mM) were used as starting materials, 14.2 g of the title compound was prepared.

Example 5: Preparation of 2-Chloro-8-Methoxy-4-(1-Methyl-1,2,3,4-Tetrahydroisoquinoline-2-Yl) Quinazoline In accordance with the same procedures as in Example 1, except that 3.35 g of the compound(14.6 mM) prepared in Preparation 2-2 and 2.15 g of the compound(14.6 mM) prepared in Preparation 1-1 were used as starting materials, 3.5 g of the title compound was prepared.

Example 6: Preparation of (R)-2-Chloro-8-Methoxy-4-(1-methyl-1,2,3,4-Tetrahydroisoquinoline-2-Yl)Quinazoline In accordance with the same procedures as in Example 1, except that 3.0 g of the compound(15.1 mM) prepared in Preparation 2-2 and 2.22 g of the compound(15.1 mM) prepared in Preparation 1-2 were used as starting materials, 3.64 g of the title compound was prepared.

Example 7: Preparation of (S)-2-Chloro-8-Methoxy-4-(1-Methyl-1,2,3,4-Tetrahydroisoquinoline-2-Yl)Quinazoline In accordance with the same procedures as in Example 1, except that 3.0 g of the compound(15.1 mM) prepared in Preparation 2-2 and 2.22 g of the compound(15.1 mM) prepared in Preparation 1-3 were used as starting materials, 3.5 g of the title compound was prepared.

Example 8: Preparation of 2-Chloro-8-Methoxy-4-(1-Trifluoromethyl-1,2,3,4-Tetrahydroisoquinoline-2-Yl) Quinazoline To a mixture of 3.05 g of the compound(13.3 mM) prepared in Preparation 2-2 and 20 ml of dimethylformamide, 2.68 g of the compound(13.3 mM) prepared in Preparation 1-5 was added and reacted at 110° C. for an hour. The reaction mixture was cooled, diluted with dichloromethane, washed with water, dried over anhydrous sodium sulfate and concentrated under a reduced pressure. The residue produced was purified by column chromatography to give 2.1 g of the title compound.

Example 9: Preparation of 2-Chloro-8-Methoxy-4-(1-Fluoromethyl-1,2,3,4-Tetrahydroisoquinoline-2-Yl) Quinazoline In accordance with the same procedures as in Example 1, except that 5.0 g of the compound(22 mM) prepared in Preparation 2-2 and 4 g of the compound(24 mM) prepared in Preparation 1-6 were used as starting materials, 6.8 g of the title compound was prepared.

Example 10: Preparation of 2-Chloro-8-Methoxy-4-(1-Ethyl-1,2,3,4-Tetrahydroisoquinoline-2-Yl) Quinazoline In accordance with the same procedures as in Example 1, except that 3.5 g of the compound(15.3 mM) prepared in Preparation 2-2 and 2.46 g of the compound(15.3 mM) prepared in Preparation 1-7 were used as starting materials, 4.07 g of the title compound was prepared.

Example 11: Preparation of 2-Chloro-8-Methoxy-4-(1-Cyclopropyl-1,2,3,4-Tetrahydroisoquinoline-2-Yl) Quinazoline In accordance with the same procedures as in Example 1, except that 1.44 g of the compound(6.30 mM) prepared in Preparation 2-2 and 1.15 g of the compound(6.9 mM) prepared in Preparation 1-8 were used as starting materials, 2.25 g of the title compound was prepared.

Example 12: Preparation of 2-Chloro-8-Methoxy-4-(3-Methyl-1,2,3,4-Tetrahydroisoquinoline-2-Yl) Quinazoline In accordance with the same procedures as in Example 1, except that 5.0 g of the compound(21.mM) prepared in Preparation 2-2 and 3.3 g of the compound(22.4 mM) prepared in Preparation 1-9 were used as starting materials, 2.0 g of the title compound was prepared.

Example 13: Preparation of 2-Chloro-8-Methoxy-4-(1,1-Dimethyl-1,2,3,4-Tetrahydroisoquinoline-2-yl) Quinazoline In accordance with the same procedures as in Example 1, except that 7.70 g of the compound(34 mM) prepared in Preparation 2-2 and 6.50 g of the compound(40 mM) prepared in Preparation 1-10 were used as starting materials, 4.9 g of the title compound was prepared.

Example 14: Preparation of 2-Chloro-8-Methoxy-4-(1,8-Dimethyl-1,2,3,4-Tetrahydroisoquinoline-2-Yl) Quinazoline In accordance with the same procedures as in Example 1, except that 3.6 g of the compound(16 mM) prepared in Preparation 2-2 and 3.10 g of the compound(19 mM) prepared in Preparation 1-11 were used as starting materials, 5.2 g of the title compound was prepared.

Example 15: Preparation of 2-Chloro-8-Methoxy-4-(1,6-Dimethyl-1,2,3,4-Tetrahydroisoquinoline-2-Yl) Quinazoline In accordance with the same procedures as in Example 1, except that 3.6 g of the compound(16 mM) prepared in Preparation 2-2 and 2.80 g of the compound(19 mM) prepared in Preparation 1-12 were used as starting materials, 5.2 g of the title compound was prepared.

Example 16: Preparation of 2-Chloro-8-Methoxy-4-(1,4-Dimethyl-1,2,3,4-Tetrahydroisoquinoline-2-Yl) Quinazoline In accordance with the same procedures as in Example 1, except that 4.65 g of the compound(20 mM) prepared in Preparation 2-2 and 3.60 g of the compound(22 mM)

prepared in Preparation 1-13 were used as starting materials, 4.5 g of the title compound was prepared.

Example 17: Preparation of 2-Chloro-8-Methoxy-4-(1,8-Ethano-1,2,3,4-Tetrahydroisoquinoline-2-Yl) Quinazoline In accordance with the same procedures as in Example 1, except that 2.64 g of the compound(11.6 mM) prepared in Preparation 2-2 and 1.85 g of the compound(11.6 mM) prepared in Preparation 1-4 were used as starting materials, 3.5 g of the title compound was prepared.

The quinazoline derivatives of formula(I) and pharmaceutically acceptable salts thereof are prepared in Examples 18–61.

Example 18: Preparation of 2-(Phenylamino)-4-(1,2,3,4-Tetrahydroisoquinoline-2-Yl)Quinazoline Hydrochloride To a mixture of 2.0 g of the compound(6.8mM) prepared in Example 1 and 15 ml of dimethylformamide, 1.25 ml of aniline(13.6 mM) was added and reacted at 110°–120° C. for 2 hours. The resultant was cooled to room temperature, neutralized by adding aqueous NaOH solution and extracted from 50 ml of dichloromethane.

The extract was dried over anhydrous sodium sulfate and concentrated under a reduced pressure. The residue produced was purified by silica gel column chromatography. The white solids produced were dissolved in 100 ml of ethyl ether, added with ethyl ether solution saturated with hydrochloride. The solids thus obtained were filtered and dried under vacuum to give 0.6 g of the title compound.

Yield: 23%

M.P: 246°–248° C.

$^1$H-NMR(DMSO-d$_6$):δ 3.1(bs, 2H), 4.18(bs, 2H), 5.16(s, 2H), 7.14–7.34(m, 5H),7.47(t, 3H), 7.62(t, 3H), 7.86(t, 1H), 8.22(d, 1H) 10.64(s, 1H)

Example 19: Preparation of 2-(N-Methylphenylamino)-4-(1,2,3,4-Tetrahydroisoquinoline-2-Yl)Quinazoline Hydrochloride In accordance with the same procedures as in Example 18, except that to a mixture of 0.9 g of the compound(3 mM) prepared in Example 1 and 15 ml of dimethylformamide, 0.4 ml of N-methylaniline(3.6 mM) was added, 0.51 g of the title compound was prepared.

Yield: 42%

M.P.: 206°–208° C.

$^1$H-NMR(CDCl$_3$): δ 2.90(t, 2H), 3.91(t, 2H), 4.00(s, 3H), 4.82(s, 2H), 6.98(d, 1H), 7.14–7.54(m, 9H), 7.75(t, 1H), 7.86(d, 1H),8.96(d, 1H), 13.8(s, 1H)

Example 20: Preparation of 2-(4-Fluoro-N-Methylphenyl-Amino)-4-(1,2,3,4-Tetrahydroisoquinoline-2-Yl)Quinazoline Hydrochloride In accordance with the same procedures as in Example 18, except that to a mixture of 2.2 g of the compound 7 mM prepared in Example 1 and 15 ml of dimethylformamide, 1.9 g of 4-fluoro-N-methylaniline(15 mM) was added, 2.45 g of the title compound was prepared.

Yield: 81%

M.P.: 242°–244° C.

$^1$H-NMR(DMSO-d$_6$): δ 2.96(t, 2H), 3.71(s, 3H), 4.01(t, 2H), 5.03(s, 2H), 7.23 (m, 4H), 7.25–7.62(m, 5H), 7.84(t, 1H), 8.20(t, 2H), 12.70 (bd, 1H)

Example 21: Preparation of 2-(2-Methylphenylamino)-4-(1,2,3,4-Tetrahydroisoquinoline-2-Yl)Quinazoline Hydrochloride In accordance with the same procedures as in Example 18, except that to a mixture of 3.05 g of the compound (10.3 mM) prepared in Example 1 and 15 ml of dimethylformamide, 2.2 ml of 2-methylaniline(20.6 mM) was added, 0.9 g of the title compound was prepared.

Yield: 22%

M.P.: 206°–209° C.

$^1$H-NMR(DMSO-d$_6$): δ 2.35(s, 3H),3.30(bs, 2H),4.17(bs, 2H),5.17(s, 2H),7.1–7.8(m, 10H), 7.9(t, 1H), 8.3(t, 1H), 10.1(s, 1H)

Example 22: Preparation of 2-(4-Fluoro-2-Methylphenyl -Amino)-4-(1,2,3,4-Tetrahydroisoquinoline-2-Yl)Quinazoline Hydrochloride In accordance with the same procedures as in Example 18, except that to a mixture of 2.2 g of the compound(7 mM) prepared in Example 1 and 15 ml of dimethylformamide, 1.7 ml of 4-fluoro-2-methylaniline(15 mM) was added, 1.35 g of the title compound was prepared.

Yield: 46%

M.P.: 210°–212° C.

$^1$HNR(DMSO-d$_6$+TFA-d): δ 2.33(s, 3H), 3.02(t, 2H), 4.10(t, 2H), 5.09(s, 2H), 7.25(m, 6H), 7.47(t, 1H), 7.58(m, 2H), 7.86(t, 1H), 8.20(d, 1H), 10.10(s, 1H), 13.25(bd, 1H)

Example 23: Preparation of 2-(4-Fluorophenylamino)-4-(1,2,3,4-Tetrahydroisoquinoline-2-Yl)Quinazoline Hydrochloride In accordance with the same procedures as in Example 18, except that to a mixture of 3.0 g of the compound. (10.1 mM) prepared in Example 1 and 20 ml of dimethylformamide, 1.9 ml of 4-fluoroaniline(20.2 mM) was added, 1.05 g of the title compound was prepared.

Yield: 26%

M.P.: 269°–271° C.

$^1$H-NMR(DMSO-d$_6$): δ 3.06(t, 2H),4.15(t, 2H),5.14(s, 2H),7.16–7.40(m, 6H), 7.46(t, 1H), 7.63(m, 3H), 7.85 (t, 1H), 8.21(d, 1H),10.70(s, 1H)

Example 24: Preparation of 2-(N-Methylphenylamino)-4-(1-Methyl-1,2,3,4-Tetrahydroisoquinoline-2-Yl)Quinazoline Hydrochloride In accordance with the same procedures as in Example 18, except that to a mixture of 1.4 g of the compound (4.52 mM) prepared in Example 2 and 15 ml of dimethyl-formamide, 1.1 ml of N-methylaniline(10.1 mM) was added, 1.02 g of the title compound was prepared.

Yield: 54%

M.P.: 213°–215° C.

$^1$H-NMR(DMSO-d$_6$): δ 1.23–1.64(m, 2H), 2.69–3.30(m, 2H), 3.44–3.75(m, 1H), 3.98(s, 3H), 4.26–4.47(m, 1H), 5.23–5.40(m, 1H), 7.17–7.56 (m, 2H),7.70–7.83(m, 9H), 8.94(d, 1H), 13.88(s, 1H)

Example 25: Preparation of 2-(4-Fluorophenylamino)-4-(1-Methyl-1,2,3,4-Tetrahydroisoquinoline-2-Yl)Quinazoline Hydrochloride In accordance with the same procedures as in Example 18, except that to a mixture of 1.26 g of the compound (4.07 mM) prepared in Example 2 and 15 ml of dimethylformamide, 0.81 ml of 4-fluoroaniline(8.54 mM) was added, 1.59 g of the title compound was prepared.

Yield: 93%

M.P.: 250°–252° C.

$^1$H-NMR(CDCl$_3$): δ 1.68–1.87(m, 3H), 2.96–3.42(m, 2H), 3.74–3.88(m, 1H), 4.64–4.72(m, 1H), 5.67–5.73 (m, 1H), 7.03–7.96(m, 12H), 10.65(s, 1H), 13.84(s, 1H)

Example 26: Preparation of 2-(4-Fluoro-2-Methylphenyl-Amino)-4-(1-Methyl-1,2,3,4-Tetrahydroisoquinoline-2-Yl) Quinazoline Hydrochloride In accordance with the same procedures as in Example 14, except that to a mixture of 1.61 g of the compound (5.20 mM) prepared in Example 2 and 15 ml of dimethylformamide, 0.89 ml of 4-fluoro-2-methylaniline(10.9 mM) was added, 1.76 g of the title compound was prepared.

Yield: 78%

M.P.: 260°–263° C.

$^1$H-NMR(CDCl$_3$): δ 1.54–1.82(m, 3H), 2.43(s, 3H), 2.85–3.38(m, 2H), 3.61–3.37 (m, 1H), 4.52–4.65(m, 1H), 5.60(q, 1H), 6.90–7.07(m, 3H), 7.17–7.27(m, 3H), 7.34–7.50(m, 2H), 7.67–7.78(m, 2H), 7.89(d, 1H), 10.02(s, 1H), 14.18(s, 1H)

Example 27: Preparation of 2-(4-Fluoro-2-Methylphenyl- Amino)-4-(1,8-Ethano-1,2,3,4-Tetrahydroisoquinoline-2-Yl) Quinazoline Hydrochloride In accordance with the same procedures as in Example 18, except that to a mixture of 1.50 g of the compound (4.46 mM) prepared in Example 3 and 15 ml of dimethylformamide, 0.80 ml of 4-fluoro-2-methylaniline(9.79 mM) was added, 1.64 g of the title compound was prepared.

Yield: 79%

M.P.: 248°–250° C.

$^1$H-NMR(CDCl$_3$): δ 1.55–1.78(m, 1H,), 2.33(s, 3H), 2.53–2.99(m, 4H), 3.82–4.02(m,1H), 4.37–4.50(m, 1H), 5.02–5.30(m, 1H), 6.60–7.01 (m, 5H), 7.43(t, 1H), 7.59–7.67(m, 2H), 7.86(t, 1H), 8.14(d, 1H), 10.13(s, 1H), 13.40(s, 1H)

Example 28: Preparation of 8-Methoxy-2-(phenylamino)-4-(1,2,3,4-Tetrahydroisoquinoline-2-Yl)Quinazoline Hydrochloride In accordance with the same procedures as in Example 18, except that to a mixture of 1.5 g of the compound (4.6 mM) prepared in Example 4 and 15 ml of dimethylform-amide, 0.65 ml of aniline(6.9 mM) was added, 1.40 g of the title compound was prepared.

Yield: 73%

M.P.: 181°–183° C.

$^1$H-NMR(DMSO-d$_6$): δ 3.14(t,2H),4.06(s, 3H),4.23(t, 2H),5.14(s, 2H),7.05–7.40 (m, 9H), 7.50(d, 1H), 7.74 (d, 2H), 11.90(s, 1H), 12.89(s, 1H)

Example 29: Preparation of 8-Methoxy-2-(N-Methylphenyl-Amino)-4-(1,2,3,4-Tetrahydroisoquinoline-2-Yl)Quinazoline Hydrochloride In accordance with the same procedures as in Example 18, except that to a mixture of 2.0 g of the compound. (6.14 mM) prepared in Example 4 and 15 ml of dimethylformamide, 1.46 ml of N-methylaniline(12.28 mM) was added, 1.5 g of the title compound was prepared.

Yield: 56%

M.P.: 90°–92° C.

H-NMR(DMSO-d$_6$): δ 3.12(t, 2H), 3.83(s, 3H), 3.96(s, 3H), 4.24(t, 2H), 5.15(s, 2 H),7.10–7.26(m, 5H), 7.28–7.72(m, 7H)

Example 30: Preparation of 8-Methoxy-2-(4-Fluorophenyl-Amino)-4-(1,2,3,4-Tetrahydroisoquinoline-2-Yl)Quinazoline Hydrochloride In accordance with the same procedures as in Example 18, except that to a mixture of 1.5 g of the compound (4.6 mM) prepared in Example 4 and 15 ml of dimethyl-formamide, 0.85 ml of 4-fluoroaniline(9.2 mM) was added, 1.3 g of the title compound was prepared.

Yield: 65%

M.P.: 239°–241° C.

$^1$H-NMR(DMSO-d$_6$): δ 3.12(t, 2H), 4.07(s, 3H), 4.20(t, 2H), 5.12(s, 2H), 6.98–7.49 (m, 3H), 7.40–7.68(m, 8H), 11.80(bs, 1H)

Example 31: Preparation of 8-Methoxy-2-(4-Fluoro-2-Methyl -Phenylamino)-4-(1,2,3,4-Tetrahydroisoquinoline-2-yl) Quinazoline Hydrochloride In accordance with the same procedures as in Example 18, except that to a mixture of 3.26 g of the compound (10 mM) prepared in Example 4 and 15 ml of dimethyl-formamide, 1.7 ml of 4-fluoro-2-methylaniline(20 mM) was added, 2.5 g of the title compound was prepared.

Yield: 55%

M.P.: 195–197° C.

$^1$H-NMR(DMSO-d$_6$): δ 2.42(s, 3H), 3.01(t, 2H), 4.09(t, 2H), 4.10(s, 3H), 5.00(s, 2H), 6.80–7.56(m, 11H), 11.20(s, 1H)

Example 32: Preparation of 8-Methoxy-2-(4-Fluoro-N-Methyl-Phenylamino)-4-(1,2,3,4-Tetrahydroisoquinoline-2-Yl) Quinazoline Hydrochloride In accordance with the same procedures as in Example 18, except that to a mixture of 2.0 g of the compound (6.14 mM) prepared in Example 4 and 15 ml of dimethyl-formamide, 1.5 g of 4-fluoro-N-methylaniline(12.2 mM) was added, 1.05 g of the title compound was prepared.

Yield: 38%

M.P.: 93°–95° C.

$^1$H-NMR(DMSO-d$_6$): δ 3.08(t, 2H), 3.88(s, 3H), 4.01(s, 3H), 4.16(t, 2H), 5.06(bs, 2H), 7.08–7.60(m, 1H)

Example 33: Preparation of 8-Methoxy-2-(4-Fluorophenyl-Amino)-4-(1-Methyl-1,2,3,4-Tetrahydroisoquinoline-2-Yl) Quinazoline Hydrochloride In accordance with the same procedures as in Example 18, except that to a mixture of 1.50 g of the compound (4.41 mM) prepared in Example 5 and 15 ml of dimethylformamide, 0.88 ml of 4-fluoroaniline(9.27 mM) was added, 0.97 g of the title compound was prepared.

Yield: 49%

M.P.: 155°–157° C.

$^1$H-NMR(CDCl$_3$): δ 1.58–1.98(m, 3H), 2.85–3.46(m, 2H), 3.73–3.97(m, 1H), 4.07(s, 3H), 4.64–4.77(m, 1H), 5.73(q, 1H), 7.03–7.67(m, 11H), 11.85(s, 1H), 12.82(s, 1H)

Example 34: Preparation of 8-Methoxy-2-(4-Fluoro-2-Methyl-Phenylamino)-4-(1-Methyl-1,2,3,4-Tetrahydroisoquinoline-2-Yl)Quinazoline Hydrochloride In accordance with the same procedures as in Example 8, except that to a mixture of 1.50 g of the compound (4.41 mM) prepared in Example 5 and 15 ml of dimethylformamide, 0.75 ml of 4-fluoro-2-methylaniline(9.27 mM) was added, 0.78 g of the title compound was prepared.

Yield: 38%

M.P.: 231°–233° C.

$^1$H-NMR(CDCl$_3$): δ 1.51–1.90(m, 3H), 2.42(s, 3H), 2.84–3.35(m, 2H), 3.57–3.81 (m, 1H), 4.10(s, 3H, 4.51–4.66(m, 1H), 5.58(q, 1H), 6.89–7.44 (m, 11H), 11.12(s, 1H, 13.16(s, 1H)

Example 35: Preparation of (R)-8-Methoxy-2-(4-Fluoro-2-Methylphenylamino)-4-(1-Methyl-1,2,3,4-Tetrahydroisoquinoline-2-Yl)Quinazoline Hydrochloride In accordance with the same procedures as in Example 18, except that to a mixture of 2.64 g of the compound (7.77 mM) prepared in Example 6 and 15 ml of dimethylformamide, 1.33 ml of 4-fluoro-2-methylaniline(16.3 mM) was added, 1.50 g of the title compound was prepared.

Yield: 42%

M.P.: 230°–233° C.

$^1$H-NMR(CDCl$_3$): δ 1.51–1.90(m, 3H), 2.42(s, 3H), 2.84–3.35(m, 2H), 3.57–3.81 (m, 1H), 4.10(s, 3H), 4.51–4.66(m, 1H), 5.58(q, 1H), 6.89–7.44 (m, 11H), 11.12(s, 1H), 13.16(s, 1H)

Example 36: Preparation of (S)-8-Methoxy-2-(4Fluoro-2-Methylphenylamino)-4-(1-Methyl-1,2,3,4-Tetrahydroisoquinoline-2-Yl)Quinazoline Hydrochloride In accordance with the same procedures as in Example 18, except that to a mixture of 2.64 g of the compound (7.77 mM) prepared in Example 7 and 15 ml of dimethylformamide, 1.33 ml of 4-fluoro-2-methylaniline(16.3 mM) was added, 1.60 g of the title compound was prepared.

Yield: 44%

M.P.: 230°–232° C.

$^1$H-NMR(CDCl$_3$): δ 1.51–1.90(m, 3H), 2.42(s, 3H), 2.84–3.35(m, 2H), 3.57–3.81 (m, 1H), 4.10(s, 3H), 4.51–4.66(m, 1H), 5.58(q, 1H), 6.89–7.44 (m, 11H), 11.12(s, 1H), 13.16(s, 1H)

Example 37: Preparation of 8-(2-Hydroxyethyloxy)-2-(4-Fluoro-2-Methylphenylamino)-4-(1-Methyl-1,2,3,4-Tetrahydroisoquinoline-2-Yl)Quinazoline Step 1: Preparation of 8-Hydroxy-2-(4-Fluoro-2-Methyl-Phenylamino)-4-(1-Methyl-1,2,3,4-Tetrahydroisoquinoline-2-Yl)Quinazoline To a mixture of 4.1 g of the compound(9.6 mM) prepared in Example 34 and 50 ml of dichloromethane, 48 ml of tribromoboran was added at 0° C. The resultant was stirred at room temperature for 14 hours and then poured into ice water. The solids produced were filtered, dissolved in dichloromethane, and neutralized by adding aqueous NaOH solution. The dichloromethane layer was separated, dried over anhydrous sodium sulfate and concentrated to give 2.4 g of the title compound.

Yield: 60%

$^1$H-NMR(DMSO-d$_6$): δ 1.48(m, 3H), 2.07(s, 3H), 2.59(t, 1H), 3.00(m, 1H), 3.42(t, 1H), 5.58(q, 1H), 6.80–7.20 (m, 9H), 7.40(d, 1H), 9.40(s, 1H), 11.40(s, 1H)

Step 2: Preparation of 8-(Ethoxycarbonylmethyloxy)-2-(4-Fluoro-2-Methylphenylamino)-4-(1-Methyl-1,2,3,4-Tetrahydroisoquinoline- 2-Yl)Quinazoline To a mixture of 0.2 g of 65% sodium hydride(5.8 mM) and 15 ml of dimethylformamide, 2.4 g of the compound(5.8 mM) prepared in Step 1 above was dropwise added at 0° C., followed by stirring 30 minutes. Then, 0.65 ml of ethylbromo acetate(5.8 mM) was dropwise added thereto and stirred for an hour. The resultant was added with water and neutralized by adding sodium bicarbonate. After extracting the resultant from dichloromethane, the dichloromethane layer was dehydrated and concentrated. The residue was purified by dried silica gel column chromatography using ethyl acetate:hexane(1:2), to give 2.0 g of the title compound.

Yield: 70%.

$^1$H-NMR(DMSO-d$_6$): δ 1.30(t, 3H), 1.48(m, 3H), 2.07(s, 3H), 2.59(t, 1H), 3.00(m, 1H), 3.42(t, 1H), 4.30(q, 2H), 4.85(s, 2H), 5.58(q, 1H), 6.80–7.20(m, 9H), 7.40(d, 1H), 9.40(s, 1H),

Step 3: Preparation of 8-(2-Hydroxyethyloxy)-2-(4-Fluoro-2-Methylphenylamino)-4-(1-Methyl-1,2,3,4-Tetrahydroisoquinoline-2-Yl)Quinazoline To a mixture of 0.12 g of lithium aluminium hydride (3.0 mM) and 30 ml of tetrahydrofuran, 1.5 g of the compound (3.0 mM) prepared in Step 2 dissolved in tetrahyrofuran was dropwise added at 0° C. and stirred for an hour. The reaction solution was added with water and extracted from dichloromethane. The dichloromethane layer was dehydrated, concentrated and purified by silica gel column chromatography, to give 0.80 g of the title compound.

Yield: 58%

M.P.: 120°–122° C.

$^1$H-NMR(DMSO-d$_6$): δ 1.48(m, 3H), 2.07(s, 3H), 2.59(t, 1H), 3.00(m, 1H), 3.42(t, 1H), 3.90–4.20(m, 4H), 5.58 (q, 1H), 6.80–7.20(m, 9H), 7.40(d, 1H), 9.40(s, 1H)

Example 38: Preparation of 2-(4-Fluoro-2-Methylphenyl-Amino)-8-Ethoxy-4-(1-Methyl-1,2,3,4-Tetrahydroisoquinoline-2-Yl)Quinazoline Hydrochloride To a mixture of 0.2 g of 65% sodium hydride(5.8 mM) and 15 ml of dimethylformamide, 2.0 g of the compound (4.8 mM) prepared in Step 1 of Example 37 was dropwise added at 0° C., followed by stirring 30 minutes. Then, a mixture of 0.4 ml of iodoethane(4.8 mM) and 5 ml of dimethylformamide was dropwise added thereto and stirred at room temperature for 2 hours. The resultant was added with water and neutralized by adding sodium bicarbonate. After extracting the resultant from ethyl acetate, the ethyl acetate layer was dehydrated and concentrated. The residue was purified by silica gel column chromatography, and dissolved in ethyl ether; and hydrochloric acid was added thereto. The solid produced were filtered and dried under vaccum, to give 0.52 g of the title compound.

Yield: 22%

M.P.: 165°–170° C.

1H-NMR(CDCl3) :δ 1.54–1.76(m, 6H), 2.40(s, 3H), 2.80–3.32(m, 2H), 3.54–3.80 (m, 1H), 4.28(q, 2H), 4.48–4.62(m, 1H), 5.52(q, 1H), 6.92–7.04(m, 3H), 7.15–7.41(m, 7H), 11.22(s, 1H), 13.00(s, 1H)

Example 39: Preparation of 2-(4-Fluoro-2-Methylphenyl-Amino-8-(Methylthiomethyloxy)-4-(1-Methyl-1,2,3,4-Tetrahydroisoquinoline-2-Yl) Quinazoline Hydrochloride In accordance with the same procedures as in Example 38, except that 0.2 g of 65% of sodium hydride(5.8 mM), 2.0 g of the compound(4.8 mM) prepared in Step 1 of Example 37 and 0.4 ml methylthiomethylchloride(4.8 mM) were used as starting materials, 0.52 g of the title compound was prepared.

Yield: 7.1%

M.P.: 94°–96° C.

1H-NMR(CDCl3) :δ 1.65–1.76(d, 3H), 2.32(s, 6H), 2.76 (d, 1H), 3.30(m, 1H), 3.60 (t, 1H), 4.38(m, 1H), 5.42 (m, 3H), 6.68(s, 1H), 6.90(d, 2H), 7.00–7.20(m, 5H), 7.50(d, 1H), 7.92(m, 1H)

Example 40: Preparation of 8-Methoxy-2-(N-Methylphenyl-Amino)-4-(1-Methyl-1,2,3,4-Tetrahydroisoquinoline-2-Yl) Quinazoline Hydrochloride In accordance with the same procedures as in Example 18, except that to a mixture of 8.00 g of the compound (8.82 mM) prepared in Example 5 and 15 ml of dimethyl-formamide, 2.00 ml of N-methyl aniline(18.45 mM) was added, 0.85 g of the title compound was prepared.

Yield: 22%

M.P.: 93°–95° C.

$^1$H-NMR(CDCl$_3$) :δ 1.63(bs, 3H), 2.80 –3.36(m, 2H), 3.50–4.00(m, 1H), 4.47–4.57(m, 1H), 5.59–5.69(m, 1H), 7.21–7.68(m, 12H), 10.44(s, 1H)

Example 41: Preparation of 8-Methoxy-2-(4-Fluoro-N-methyl- Phenylamino)-4-(1-Methyl-1,2,3, 4-Tetrahydroisoquinoline-2-Yl)Quinazoline Hydrochloride In accordance with the same procedures as in Example 18, except that to a mixture of 1.00 g of the compound (2.94 mM) prepared in Example 5 and 15 ml of dimethyl-formamide, 0.77 g of 4-fluoro-N-methyl aniline(6.18 mM) was added, 0.66 g of the title compound was prepared.

Yield: 44%

M.P.: 100°–103° C.

$^1$H-NMR(CDCl$_3$): δ 1.58–1.82(m, 1H), 2.82–3.61(m, 2H), 3.67–4.05(m, 1H), 4.51–4.64(m, 1H), 5.51–5.63 (m, 1H), 7.00–7.13(m, 1 H), 9.80(bs, 1H)

Example 42: Preparation of 2-(4-Fluoro-2-Methylphenyl-Amino)-8-Methoxy-4-(1-Trifluoromethyl-1,2,3,4-Tetrahydroisoquinoline-2-Yl)Quinazoline Hydrochloride In accordance with the same procedures as in Example 18, except that to a mixture of 1.9 g of the compound (4.82 mM) prepared in Example 8 and 15 ml of dimethyl-formamide, 0.82 ml of 4-fluoro-2-methyl aniline( 10.1 mM) was added, 1.32 g of the title compound was prepared.

Yield: 53%

M.P.: 158°–160° C.

1H-NMR(CDCl3) :δ 2.38(s, 3H), 2.97–3.30(m, 2H), 3.98–4.18(m, 4H), 4.65–4.82 (m, 1H), 6.301(q, 1H), 6.85–7.00(m, 2H), 7.15–7.38(m, 7H), 7.50(d, 1H), 11.40(s, 1H), 14.40(s, 1H), 14.55(s, 1H)

Example 43: Preparation of 2-(4-Fluorophenylamino)-8-Methoxy-4-(1-Fluoromethyl-1,2,3,4-Tetrahydroisoquinoline-2-Yl)Quinazoline Hydrochloride In accordance with the same procedures as in Example 18, except that to a mixture of 3.3 g of the compound (9 mM) prepared in Example 9 and 15 ml of dimethylform-amide, 1.9 ml of 4-fluoroaniline(20.0 mM) was added, 0.61 g of the title compound was prepared.

Yield: 14.5%

M.P..: 208°–211° C.

1H-NMR(CDCl3) :δ 3.02(bd, 1H), 3.25(m, 1H), 3.94(bd, 1H), 4.06(s, 3H), 4.74(d, 2H), 5.00(m, 1H), 6.02(tt, 1H), 7.08(t, 2H), 7.20(m, 6H), 7.58(m, 3H), 11.90(s, 1H), 12.96(s, 1H)

Example 44: Preparation of 2-(4-Fluoro-2-Methylphenyl-Amino)-8-Methoxy-4-(1-Fluoromethyl-1,2,3,4-Tetrahydroisoquinoline-2-Yl) Quinazoline Hydrochloride In accordance with the same procedures as in Example 18, except that to a mixture of 3.3 g of the compound (9.0 mM) prepared in Example 9 and 15 ml of dimethylform-amide, 2.2 ml of 4-fluoro-2-methylaniline(20 mM) was added, 0.65 g of the title compound was prepared.

Yield: 15%

M.P.: 122°–130° C.

1H-NMR(CDCl3) :δ 2.40(s, 3H), 2.84–2.95(bd, 2H), 3.15(bd, 1H), 4.86(bd, 1H), 4.10(s, 3H), 4.62(bd, 1H), 4.64–4.88(dd, 2H), 5.80(tt, 1H), 6.90–7.08(m, 3H), 7.19–7.40(m, 6H), 7.62(d, 1H)

Example 45: Preparation of 8-Methoxy-2-(4-Fluorophenyl-Amino)-4-(1-Ethyl-1,2,3,4-Tetrahydroisoquinoline-2-Yl) Quinazoline Hydrochloride In accordance with the same procedures as in Example 18, except that to a mixture of 1.50 g of the compound (4.63 mM) prepared in Example 10 and 15 ml of dimethyl-formamide, 0.65 ml of 4-fluoroaniline(6.95 mM) was added, 1.20 g of the title compound was prepared.

Yield: 56%

M.P.: 187°–189° C.

$^1$H-NMR(DMSO-d$_6$): δ 0.82(t, 3H), 1.90(bs, 1H), 2.08 (m, 1H), 3.10(m,3H), 4.02(s, 3H), 4.15(bs, 1H), 4.51 (m, 1H), 5.70(t, 1H), 7.20–7.80(m, 11H), 11.20(s, 1H), 12.05(s, 1H)

Example 46: Preparation of 8-Methoxy-2-(2-Methyl-4-Fluoro-Phenylamino)-4-(1-Ethyl-1,2,3,4-Tetrahydroisoquinoline-2-Yl)Quinazoline Hydrochloride In accordance with the same procedures as in Example 18, except that to a mixture of 1.5 g of the compound (4.63 mM)

prepared in Example 10 and 15 ml of dimethyl-formamide, 0.80 ml of 2-methyl-4-fluoroaniline(9.73 mM) was added, 0.70 g of the title compound was prepared.

Yield: 32%

M.P.: 145°–147° C.

$^1$H-NMR(DMSO-$d_6$): δ 0.66(t, 3H), 1.72(bs, 1H), 1.94 (m, 1H), 2.32(s, 3H), 3.06 (m, 3H), 3.96–4.20(bs+s, 4H), 4.40(m, 1H), 5.45(t, 1H), 7.00–7.80(m, 10H), 10.58(bs, 1H), 12.42(bs, 1H)

Example 47: Preparation of 2-(4-Fluoro-2-Methylphenyl-Amino)-8-Methoxy-4-(1-cyclopropyl-1,2,3,4-Tetrahydroisoquinoline-2-Yl)Quinazoline Hydrochloride In accordance with the same procedures as in Example 18, except that to a mixture of 2.25 g of the compound (6.15 mM) prepared in Example 11 and 15 ml of dimethyl-formamide, 1.05 ml of 4-fluoro-2-methylaniline(12.9 mM) was added, 2.15 g of the title compound was prepared.

Yield: 71%

M.P.: 134°–136° C.

1H-NMR(CDCl3) :δ 0.10–0.50(m, 3H), 0.52–0.66(m, 1H), 1.16–1.36(m, 1H), 2.39 (s, 1H), 3.00–3.40(m, 2H), 4.08–4.25(m, 4H), 4.50–4.70(m, 1H), 5.36(d, 1H), 6.87–7.05(m, 3H), 7.16–7.36(m, 6H), 7.48 (d, 1H), 11.10(d, 1H), 13.04(s, 1H)

Example 48: Preparation of 2-(4-Fluorophenylamino)-8-Methoxy-4-(3-Methyl-1,2,3,4-Tetrahydroisoquinoline-2-Yl) Quinazoline Hydrochloride In accordance with the same procedures as in Example 18, except that to a mixture of 1.5 g of the compound (4.4 mM) prepared in Example 12 and 15 ml of dimethyl-formamide, 0.7 ml of 4-fluoroaniline(6.6 mM) was added, 0.7 g of the title compound was prepared.

Yield: 35%

M.P.: 150°–153 C.

$^1$H-NMR(CDCl3) :δ 1.38(d, 3H), 2.80(d, 1H), 3.37(d, 1H), 4.08 (s, 3H), 4.92(d, 1H), 5.30(m, 2H), 6.90–7.40 (m, 8H), 7.40–7.70(m, 3H), 11.90(s, 1H), 12.80(s, 1H)

Example 49: Preparation of 2-(4-Fluoro-2-Methylphenyl-Amino)-8-Methoxy-4-(3-Methyl-1,2,3,4-Tetrahydroisoquinoline-2-Yl)Quinazoline Hydrochloride In accordance with the same procedures as in Example 18, except that to a mixture of 2.0 g of the compound (5.9 mM) prepared in Example 12 and 15 ml of dimethyl-formamide, 1.1 ml of 4-fluoro-2-methylaniline(8.9 mM) was added, 0.8 g of the title compound was prepared.

Yield: 29%

M.P.: 214°–217° C.

1H-NMR(CDCl3) :δ 1.30(d, 3H), 2.40(s, 3H), 2.70(d, 1H), 3.22 (d, 1H), 4.10(s, 3H), 4.86(m, 1H), 5.10–5.30 (m, 2H), 6.90–7.50(m, 10H), 11.20(s, 1H), 13.20(s, 1H)

Example 50: Preparation of 2-(4-Fluorophenylamino)-8-Methoxy-4-(1,1-Dimethyl-1,2,3,4-Tetrahydroisoquinoline-2-Yl)Quinazoline Hydrochloride In accordance with the same procedures as in Example 18, except that to a mixture of 1.80 g of the compound (5.0 mM) prepared in Example 13 and 10 ml of dimethyl-formamide, 1.10 ml of 4-fluoroaniline(11 mM) was added, 1.14 g of the title compound was prepared.

Yield: 49%

M.P.: 134°–138° C.

1H-NMR(CDCl3) :δ 1.75(s, 6H), 3.22(t, 2H), 4.00(t, 2H), 4.09(s, 3H), 7.13(m, 6H), 7.25(m, 2H), 7.40(m, 3H), 11.62(s, 1H), 13.08(s, 1H)

Example 51: Preparation of 2-(4-Fluoro-2-Methylphenyl-1-Amino)-8-Methoxy-4-(1,1-Dimethyl-1,2,3,4-Tetrahydroisoquinoline-2-Yl) Quinazoline Hydrochloride In accordance with the same procedures as in Example 18, except that to a mixture of 1.80 g of the compound (5.0 mM) prepared in Example 13 and 10 ml of dimethyl-formamide, 1.20 ml of 4-fluoro-2-methylaniline(11 mM) was added, 0.81 g of the title compound was prepared.

Yield: 34%

M.P.: 176°–180° C.

1H-NMR(CDCl3) :δ 1.56(s, 6H), 2.36(s, 3H), 3.21(t, 2H), 3.98(t, 2H), 4.11(s, 3H), 6.94(m, 2H), 7.16–7.38(m, 8H), 11.22(s, 1H), 13.40(s, 1H)

Example 52: Preparation of 2-(4-Fluorophenylamino)-8-Methoxy-4-(1,8-Dimethyl-1,2,3,4-Tetrahydroisoquinoline-2-Yl)Quinazoline Hydrochloride In accordance with the same procedures as in Example 18, except that to a mixture of 3.3 g of the compound(9 mM) prepared in Example 14 and 15 ml of dimethylformamide, 1.9 ml of 4-fluoroaniline(20 mM) was added, 1.14 g of the title compound was prepared.

Yield: 49%

M.P.: 134°–138° C.

1H-NMR(CDCl3) :δ 1.74(s, 3H), 1.23(d, 3H), 2.82–3.37 (m, 2H), 3.68–3.84(m, 1H), 4.05(s, 3H), 4.58–4.80(m, 1H), 5.66(q, 1H), 6.90–7.32 (m, 7H), 7.45(d, 1H), 7.58–7.66(m, 2H), 11.20(s, 1H)

Example, 53: Preparation of 2-(4-Fluoro-2-Methylphenyl-Amino)-8-Methoxy-4-(1,8-dimethyl-1,2,3,4-Tetrahydroisoquinoline-2-Yl)Quinazoline Hydrochloride In accordance with the same procedures as in Example 18, except that to a mixture of 2.50 g of the compound (7.06 mM) prepared in Example 14 and 15 ml of dimethyl-formamide, 1.21 ml of 4-fluoro-2-methylaniline(14.9 mM) was added, 0.70 g of the title compound was prepared.

Yield: 21%

M.P.: 128°–131° C.

$^1$H-NMR(CDCl3) :δ 1.56(s, 3H), 2.22(s, 3H), 2.31(s, 3H), 2.74–3.20(m, 2H), 3.62–3.79(m, 1H), 3.98(s, 3H), 4.36–4.52(m, 1H), 5.50(q, 1H), 6.80–7.25(m, 5H), 7.38–7.50(m, 2H), 7.53–7.77(m, 2H), 10.28(s, 1H), 12.35(s, 1H)

Example 54: Preparation of 2-(4-Fluorophenylamino)-8-Methoxy-4-(1,6-Dimethyl-1,2,3,4-Tetrahydroisoquinoline-2-Yl)Quinazoline Hydrochloride In accordance with the same procedures as in Example 18, except that to a mixture of 2.50 g of the compound (7.06 mM) prepared in Example 15 and 10 ml of dimethylformamide, 1.40 ml of 4-fluoroaniline(4.8 mM) was added, 2.0 g of the title compound was prepared.

Yield: 61%

M.P.: 124°–128° C.

1H-NMR(CDCl3) :δ 1.73(bs, 3H), 2.32(s, 3H), 2.88–3.3 g(m, 2H), 3.66–3.86(m, 1H), 4.07(s, 3H), 4.60–4.74(m, 1H), 5.70(q, 1H), 6.96–7.18 (m, 6H), 7.31 (t, 1H), 7.45(d, 1H), 7.60–7.77(m, 2H), 11.80 (s, 1H), 12.76(s, 1H)

Example 55: Preparation of 2-(4-Fluoro-2-Methylphenyl-Amino)-8-Methoxy-4-(1,6-Dimethyl-1,2,3,4-Tetrahydroisoquinoline-2-Yl)Quinazoline Hydrochloride In accordance with the same procedures as in Example 18, except that to a mixture of 2.50 g of the compound (7.06 mM) prepared in Example 15 and 10 ml of dimethylformamide, 1.21 ml of 4-fluoro-2-methylaniline(14.9 mM) was added, 1.10 g of the title compound was prepared.

Yield: 33%

M.P.: 130°–135° C.

1H-NMR(CDCl3) :δ 1.63(bs, 3H), 2.42(s, 3H), 2.70–3.30 (m, 2H), 3.31(s, 3H), 3.62–3.79(m, 1H), 3.50–3.85(m, 1H), 4.09(s, 3H), 4.50–4.62 (m, 1H), 5.55(q, 1H), 6.80–7.22(m, 6H), 7.28(t, 1H), 7.37–7.46(m, 2H), 11.11(m, 2H), 13.12(s, 1H)

Example 56: Preparation of 2-(4-Fluorophenylamino)-8-Methoxy-4-(1,4-Dimethyl-1,2,3,4-Tetrahydroisoquinoline-2-Yl)Quinazoline Hydrochloride In accordance with the same procedures as in Example 18, except that to a mixture of 3.00 g of the compound (8.40 mM) prepared in Example 16 and 10 ml of dimethylformamide, 1.90 ml of 4-fluoro-2-methylaniline(20 mM) was added, 1.10 g of the title compound was prepared.

Yield: 30%

M.P.: 145°–149° C.

1H-NMR(CDCl3) :δ 1.42(d, 3H), 1.83(bd, 3H), 3.24(bd, 2H), 4.08(s, 3H), 4.60 (bd, 1H), 5.72(q, 1H), 6.84(t, 1H), 7.10(m, 2H), 7.30(m, 6H), 7.63(m, 1H),11.80(s, 1H), 12.78(bd, 1H)

Example 57: Preparation of 2- (4-fluoro-2-Methylphenyl-Amino)-8-Methoxy-4-(1,4-Dimethyl-1,2,3,4-Tetrahydroisoquinoline-2-Yl) Quinazoline Hydrochloride In accordance with the same procedures as in Example 18, except that to a mixture of 3.10 g of the compound (8.76 mM) prepared in Example 16 and 10 ml of dimethylformamide, 2.20 ml of 4-fluoro-2-methylaniline(20 mM) was added, 1.40 g of the title compound was prepared.

Yield: 34%

M.P.: 135°–139° C.

1H-NMR(CDCl3) :δ 1.12–1.37(bd, 3H), 2.40(s, 3H), 3.20(bd, 2H), 4.12(s, 3H), 4.43(q, 1H), 5.57–5.7 6(qq, 1H), 6.95(m, 3H), 7.30(m, 5H), 7.42(m, 2H), 10.82(bd, 1H)

Example 58: Preparation of 8-Methoxy-2-(4-Fluorophenyl-Amino)-4-(1,8-Ethano-1,2,3,4-Tetrahydroisoquinoline-2-Yl)Quinazoline Hydrochloride In accordance with the same procedures as in Example 18, except that to a mixture of 1.10 g of the compound (3.10 mM) prepared in Example 17 and 15 ml of dimethylformamide, 0.5 ml of 4-fluoroaniline(4.6 mM) was added, 0.9 g of the title compound was prepared.

Yield: 63%

M.P.: 186°–196° C.

1-NMR(CDCl3): δ 1.78(m, 1H,), 2.70–3.05(m, 4H), 3.90 (m, 1H), 4.06(s, 3H), 4.48(d, 1H), 5.38(m, 1H), 7.09–7.40(m, 6H), 7.52(d, 1H), 7.70 (d, 3H), 11,18(s, 1H), 12.10(bs, 1H),

Example 59: Preparation of 8-Methoxy-2-(4-Fluoro-2-Methyl-Phenylamino)-4-(1,8-Ethano-1,2,3,4-Tetrahydroisoquinoline-2-Yl)Quinazoline Hydrochloride In accordance with the same procedures as in Example 18, except that to a mixture of 1.50 g of the compound (4.46m14) prepared in Example 17 and 15 ml of dimethylformamide, 0.80 ml of 4-fluoro-2-methylaniline(9.79 mM) was added, 1.64 g of the title compound was prepared.

Yield: 37%

M.P.: 195°–197° C.

1H-NMR(CDCl3): δ 1.60(m, 1H,), 2.33(s, 3H), 2.42–2.93 (m, 4H), 3.90(m, 1H), 4.06(s, 3H), 4.48(m, 1H), 5.10 (m, 1H), 7.10–7.80(m, 9H), 10.40(bs, 1H), 12.40(bs, 1H)

Example 60: Preparation of 2-(4-Fluoro-2-MethylPhenyl-Amino)-8-Methoxy-4-(1-Methyl-1,2,3,4-Tetrahydroisoquinoline-2-Yl)Quinazoline Methanesulfonate To a mixture of 1.20 g of the compound(2.80 mM) prepared in Example 34 and 50 ml of dichloromethane, 0.2 ml of methane sulfonate(3.08 mM) was dropwise added. The resultant was stirred at room temperature for 30 minutes and Concentrated under a reduced pressure. The residue produced was crystallized by adding ethyl ether to give 1.32 g of the title compound.

Yield: 90%

M.P.: 109°–115° C.

1H-NMR(CDCl3) :δ 1.40–1.80(m, 3H), 2.35(s, 3H), 2.93–3.40(m, 5H), 3.58–3.90 (m, 1H), 4.11(s, 3H), 4.48–4.63(m, 1H), 5.53(q, 1H), 6.89–7.04(m, 3H), 7.17–7.25(m, 4H), 7.31–7.46(m, 3H), 10.08(s, 1H), 12.43(s, 1H)

Example 61: Preparation of 2-(4-Fluoro-2-Methylphenyl-Amino)-8-Methoxy-4- (1-Methyl-1,2,3,4-Tetrahydroisoquinoline-2-Yl)Quinazoline Malate To a mixture of 0.27 g of maleic acid(2.33 mM) and 50 ml of ethanol, 1.20 g of the compound (2.80 mM) prepared in Example 34 was dropwise added. The resultant was stirred at room temperature for 12 hours and concentrated under a reduced pressure. The residue produced was crystallized by adding ethyl ether and ethyl acetate, to give 1.15 g of the title compound.

Yield: 75%

M.P.: 190°–192° C.

1H-NMR(CDCl3) :δ 1.44–1.70(m, 3H), 2.32(s, 3H), 2.8–3.2 g(m, 2H), 3.55–3.75 (m, 1H), 4.11(s, 3H), 4.43–4.60(m, 1H), 5.53(q, 1H), 6.35 (s, 3H), 6.8–7.04 (m, 3H), 7.17–7.35(m, 6H), 7.43(d, 1H), 12.00(s, 1H), 13.10(s, 1H)

EXPERIMENT 1

Inhibition of Proton Pump($H^+/K^+$ATPase) Activity

1-1: Preparation of a Proton Pump Enzyme Source

A New Zealand white rabbit was killed by blowing its head and the stomach was taken out. The contents of the stomach were removed and the stomach walls were washed with was saline. The inner wall of the stomach was scratched out with a slide glass and the cells thus obtained were homogenized in 0.25M sucrose buffer by means of a Teflon-glass homogenizer. The homogenous solution was centrifuged at 10,000 g for 10 minutes and the supernatant was further centrifuged at 20,000 g for 20 minutes. The supernatant thus obtained was centrifuged at an ultra-high speed of 180,000 g for 1 hour. The pellets precipitated were collected by discarding the supernatant and suspended in 50 mM Tris-HCl buffer having pH 7.2. The suspension was dialyzed twice with the same buffer(of 1,000 times volume) for 3 hours and stored into liquid nitrogen.

The above centrifugation and dialysis were carried out at 4° C. The microsomes thus obtained were used as an enzyme source of the in vitro enzyme reaction study of proton pump.

1-2: Measurement of Proton Pump Activity

The inhibitory effects of proton pump activity by the compounds of the present invention were measured by the in vitro enzyme reaction study. The proton pump activity stimulated by $Mg^{++}$ was used as a negative comparative group, and the activity stimulated by $Mg^{++}$ and $K^+$ was used as a positive comparative group. The comparative compound was omeprazole.

Test tubes were divided into 4 groups: Group 1 as negative comparative group(n=3), Group 2 as positive comparative group(n=3), Group 3(n=5) to be administered with the compound of the present invention and Group 4(n=5) to be administered with the comparative compound. The inhibitory effects of proton pump activity of Groups 3 and 4 were measured by employing the compound prepared in Example 34 and omeprazole, respectively, each of which was dissolved in dimethylsulfoxide at 5 different concentrations.

To each of Groups 1, 2, 3 and 4, were added 0.1 ml of magnesium chloride(40 mM) dissolved in 50 mM Tris-HCl buffer (pH 7.2) and 50 Ng of the enzyme source prepared in Experiment 1-1. Then, 0.1 ml of potassium chloride(500 mM) and 0.1 ml of ammonium chloride(100 mM) dissolved in 50 mM Tris-HCl buffer(pH 7.2) were added to all groups except for Group 1.

0.1 ml of dimethylsulfoxide was added to each of Groups 1 and 2; and to Group 3 was added 0.01 ml of the solution in which the compound prepared in Example 34 was dissolved in dimethylsulfoxide at 5 different concentrations. To Group 4, 0.01 ml of the solution prepared by dissolving omprazole in dimethylsulfoxide at 5 different concentrations (37.6, 21.4, 12.2, 7.0 and 4.0 µM) was added. 50 mM Tris-HCl buffer was added thereto so as to make the total volume 0.4 ml.

Thereafter, the test tubes of each Group were placed at 37° C. for 15 minutes for the prereaction. 0.1 ml of ATP solution(33.3 mM), which was prepared by adding Tris-ATP 50 mM to Tris-HCl buffer having pH 7.2, was added until the reaction volume became 0.5 ml. The final concentrations of $MgCl_2$, KCl, $NH_4Cl$, ATP, enzyme and Tris-HCl were 8 mM, 100 mM, 20 mM, 6.7 mM, 100µg/ml and 50 mM, respectively. After the reaction was carried out at 37° C. for 30 minutes, 25% cold trichloroacetic acid was added to terminate the enzyme reaction. The released inorganic phosphate was measured by an automatic analyzer(SBA 300, Gilford).

The difference between Group 1 and Group 2 represents the proton pump activity activated by $K^+$ only. The inhibition percentages of Groups 3 and 4 were calculated from Litchfield-wilcoxon equation[see *J. Pharmacol. Exptl. Ther.* 96, 99(1949)]. The concentrations of the test compounds which inhibit 50% of the proton pump activity are represented as $IC_{50}$ in Table 1.

TABLE 1

The Inhibition (50%) of the proton pump activity

| compound | $IC_{50}$ of test compound (µM) | $IC_{50}$ of Omeprazole (µM) | Effect ratio |
|---|---|---|---|
| Example 18 | 0.6 | 37.0 | 61.67 |
| Example 19 | 5.2 | 9.5 | 1.83 |
| Example 20 | 8.4 | 9.2 | 1.10 |
| Example 21 | 1.2 | 7.4 | 6.17 |
| Example 22 | 0.7 | 7.9 | 11.29 |
| Example 23 | 2.0 | 8.6 | 4.30 |
| Example 24 | ~12.5 | 16.1 | ~1.29 |
| Example 25 | 2.7 | 16.1 | 5.88 |
| Example 26 | 0.4 | 16.1 | 46.00 |
| Example 27 | 2.9 | 5.7 | 1.97 |
| Example 28 | 1.2 | 8.3 | 6.92 |
| Example 29 | 4.9 | 7.2 | 1.47 |
| Example 30 | 2.2 | 7.2 | 3.27 |
| Example 31 | 2.0 | 10.1 | 5.13 |
| Example 32 | >16.0 | 9.3 | >0.58 |
| Example 33 | 2.3 | 2.8 | 1.22 |
| Example 34 | 1.7 | 9.2 | 5.45 |
| Example 35 | 1.8 | 5.1 | 2.83 |
| Example 36 | 4.0 | 5.1 | 1.28 |
| Example 37 | ~12.5 | 7.5 | ~0.60 |
| Example 38 | 1.2 | 2.0 | 1.67 |
| Example 39 | 4.0 | 2.8 | 0.70 |
| Example 40 | 1.3 | 10.6 | 8.15 |
| Example 41 | 3.8 | 7.6 | 2.00 |
| Example 42 | 12.5 | 2.2 | <0.18 |
| Example 43 | >12.5 | 12.1 | <0.97 |
| Example 44 | ~12.5 | 12.1 | ~0.97 |
| Example 45 | 8.9 | 4.1 | 0.46 |
| Example 46 | ~6.0 | 4.1 | 0.68 |
| Example 47 | ~25 | 12.1 | 0.49 |
| Example 48 | ~25.0 | 6.3 | ~0.25 |
| Example 49 | >25.0 | 6.3 | >0.25 |
| Example 50 | 6.05 | 7.4 | 1.22 |
| Example 51 | 6.12 | 7.4 | 1.21 |
| Example 52 | 7.5 | 9.4 | 1.26 |
| Example 53 | 2.0 | 9.4 | 4.75 |
| Example 54 | ~12.5 | 8.0 | ~0.64 |
| Example 55 | ~10.0 | 8.0 | ~0.80 |
| Example 56 | >12.5 | 7.5 | <0.60 |
| Example 57 | 7.18 | 7.5 | 1.04 |
| Example 58 | 13.6 | 8.8 | 0.65 |
| Example 59 | 4.8 | 8.5 | 1.77 |
| Example 60 | 1.8 | 9.2 | 5.20 |
| Example 61 | 2.1 | 9.2 | 4.42 |

EXPERIMENT 2

Inhibition of Gastric Secretion

In accordance with the method disclosed in Shay, H., et al., *Gastroenterology* 5, 43–61(1945), Experiment 2 was carried out.

Sprague-Dawley rats having a body weight of 170±10 g were divided into 3 groups(n=5) and deprived of food for 24 hours before the experiment with free access to water. Under ether anesthesia, the abdomen was incised, and the pylorus was ligated. As a comparative group, Group 1 was administered intraduodenally in a volume of 0.5 ml/200 g of 30% aqueous polyethylene glycol 400 solution. Groups 2 and 3 were administered intraduodenally with the compound of Example 34 and omeprazole, respectively, each of which was suspended in 30% aqueous polyethylene glycol 400 solution at a concentration of 20 mg/kg. After closing the abdominal cavity, the rats were placed for 5 hours and then killed by cervical dislocation. The stomach was extracted to obtain gastric juice.

The gastric juice was centrifuged at 1,000 g to remove precipitates. The amount and acidity of the gastric juice were measured. Relative volumes, relative acid concentrations and relative acid outputs of the test compounds were calculated from equations(I), (II) and (III) and the results are shown in Table 2.

Relative volume (I) = the average amount of gastric juice of Group 1 − the average amount of gastric juice of Group 2)/(the average amount of gastric juice of Group 1 − the average amount of gastric juice of Group 3)

Relative acid concentration (II) = (the average acidity of Group 1 − the average acidity of Group 2)/(the average acidity of Group 1 − the average acidity of Group 3)

Relative acid output (III) = (the total amount of acid output of Group 1 − the total amount of acid output of Group 2)/(the total amount of acid output of Group 1 − the total amount of acid output of Group 3).

TABLE 2

The amount and acidity of the gastric juice

| Compound | Rel. Vol. (%) | Rel. Conc. (%) | Relative Acid Output |
|---|---|---|---|
| Example 18 | 0.38 | 0.02 | 0.29 |
| Example 19 | 1.03 | 0.28 | 0.68 |
| Example 20 | 1.28 | 0.64 | 0.92 |
| Example 21 | 0.74 | −0.04 | 0.38 |
| Example 22 | 0.74 | 0.43 | 0.64 |
| Example 23 | 0.39 | 0.42 | 0.44 |
| Example 24 | 0.47 | 0.07 | 0.36 |
| Example 25 | 0.69 | 0.14 | 0.50 |
| Example 26 | 0.38 | 0.04 | 0.25 |
| Example 27 | 0.29 | 0.12 | 0.30 |
| Example 28 | 0.67 | 0.37 | 0.64 |
| Example 29 | 0.87 | 0.67 | 0.84 |
| Example 30 | 0.76 | 0.53 | 0.76 |
| Example 31 | 0.86 | 0.74 | 0.79 |
| Example 32 | 0.47 | 0.16 | 0.43 |
| Example 33 | 1.09 | 0.34 | 0.79 |
| Example 34 | 1.36 | 0.55 | 0.97 |
| Example 35 | 0.92 | 0.58 | 0.79 |
| Example 36 | 0.82 | 0.42 | 0.67 |
| Example 37 | 0.37 | 0.15 | 0.37 |
| Example 38 | 0.80 | 0.53 | 0.83 |
| Example 39 | 0.66 | 0.22 | 0.57 |
| Example 40 | 0.73 | 0.76 | 0.82 |
| Example 41 | 0.63 | 0.15 | 0.48 |
| Example 42 | 0.40 | 0.14 | 0.42 |
| Example 43 | 0.81 | 0.44 | 0.76 |
| Example 44 | 0.73 | 0.56 | 0.75 |
| Example 45 | 0.20 | −0.22 | −0.06 |
| Example 46 | 0.42 | −0.21 | 0.11 |
| Example 47 | 0.45 | 0.15 | 0.33 |
| Example 48 | 0.75 | 0.52 | 0.76 |
| Example 49 | 0.59 | 0.12 | 0.42 |
| Example 50 | 0.85 | 0.65 | 0.82 |
| Example 51 | 0.86 | 0.64 | 0.82 |
| Example 52 | 1.03 | 0.55 | 0.79 |
| Example 53 | 1.01 | 0.65 | 0.92 |
| Example 54 | 0.94 | 0.35 | 0.82 |
| Example 55 | 0.57 |  | 0.50 |
| Example 56 | 0.91 | 0.70 | 0.85 |

TABLE 2-continued

The amount and acidity of the gastric juice

| Compound | Rel. Vol. (%) | Rel. Conc. (%) | Relative Acid Output |
|---|---|---|---|
| Example 57 | 0.92 | 0.35 | 0.67 |
| Example 58 | 1.32 | 0.71 | 0.94 |
| Example 59 | 1.53 | 0.47 | 0.83 |
| Example 60 | 1.03 | 0.55 | 0.84 |
| Example 61 | 0.73 | 0.51 | 0.76 |

EXPERIMENT 3

Anti-Secretory Effects

In accordance with the method [see Ghosh and Shild, et al., *British Journal of pharmacology* 13:54–61 (1958)], anti-secretory effects of the test substances were studied in this Experiment.

3-1: Anti-Secretory Effects of the Test Substances When Gastric Secretion is Stimulated by Histamine Sprague-Dawley male rats having a body weight of 200±20 g were divided into 3 groups, Group 1 to be administered with the compound of Example 34, Group 2 to be administered with SK&F96067[see Keeling, D. J., et al., *Biochemical pharmacology* 42, 1, 123–130(1991)] and Group 3 to be administered with omeprazole. The rats of each Group, deprived of food for 24 hours before the experiment with free access to water, were anesthetized by intraperitoneally administering of 1.5 g/kg of 20% aqueous urethane solution and positioned on the test plate which was heated and maintained at 37° C. The anesthetized rats were cannulated at the right jugular vein for the administration of the test compounds and the left jugular vein for the administration of stimulating substances. After an abdominal incision, tubes were inserted into the esophagus and duodenum, each of which was connected with saline in a thermostat and a fraction collector. The esophagus and duodenum were perfused with saline at a rate of 1 ml/min from the thermostat by means of a peristaltic pump.

To the right jugular vein, were administered the compound prepared in Example 34 and, as comparative compounds, SK&F96067 and omeprazole, each of which was dissolved in ethanol, 40% polyethylene glycol or saline, respectively. To the left jugular vein, histamine was administered as a gastric secretion stimulator.

The stomach was first perfused with saline and the perfusates containing the gastric juice were collected at an interval of 10 minutes by means of the fraction collector. When the gastric secretion reached to an equilibrium state, which took more than 60 minutes, histamine was infused at a dosage of 4 mg/2 ml/200 g/hr to stimulate the gastric secretion, while collecting the perfusates for 60 minutes at an interval of 10 minutes.

While histamine was continuously being infused, the compound prepared in Example 34, SK&F96067 and omeprazole of different concentrations as represented in Table 3 were intravenously injected into the right jugular vein to Groups 1, 2 and 3, respectively; and then the perfusates were collected. The volume and acidity of the fractions collected were measured to calculate the acid output in μM/10 min.

The gastric secretion inhibition (%) of the test compounds was calculated from the following equation:

The gastric secretion inhibition (%) of the test compounds $=(A-C)/(A-B)\times 100\ldots$ (IV)

in which

A is the gastric acid output(μmol/10 min) of the fraction collected 60 mins after the administration of histamine;

B is the gastric acid output(μmol/10 min) of the fraction collected 60 minutes after the perfusion with saline; and C is the minimum gastric acid output(μmol/10min) during the period of 120 minutes after the administration of the test compounds.

The results are shown in Table 3-1.

TABLE 3-1

| | The gastric secretion inhibition (%) | | |
|---|---|---|---|
| Amount (mg/kg) | Omeprazole | SK&F96067 | Compound of Example 34 |
| 0.1 | 8.0% | | |
| 0.3 | 49.4% | | |
| 0.5 | | 29.8% | 44.4% |
| 1.0 | 102.3% | 57.1% | 52.0% |
| 3.0 | | 75.9% | 76.5% |
| $ED_{50}$ | 0.29 mg/kg | 0.96 mg/kg | 0.90 mg/kg |

3-2: Inhibition of Gastric Secretion by the Test Substances in case the Gastric Secretion is Stimulated by Pentagastrin The same procedures as in Experiment 3-1 were carried out, except that as a secretion stimulating substance, pentagastrin was infused into the left jugular vein of the rats at a dosage of 24 μg/2 ml/200 g/hr. The results of the experiment are shown in Table 3-2.

TABLE 3-2

| | The gastric secretion inhibition (5) and $ED_{50}$ when the secretion is stimulated by histamine | | |
|---|---|---|---|
| Amount (mg/kg) | Omeprazole | SK&F96067 | Compound of Example 34 |
| 0.1 | | | |
| 0.3 | 5.0% | | |
| 0.5 | 63.1% | | |
| 1.0 | 114.3% | 32.6% | 41.2% |
| 3.0 | | 64.0% | 77.0% |
| 5.0 | | 77.3% | 110.2% |
| $ED_{50}$ | 0.47 mg/kg | 1.85 mg/kg | 1.31 mg/kg |

EXPERIMENT 4

Reversibility Test 4-1: Preparation of Gastric Vesicles

Gastric vesicles were prepared from pig stomach by the method described in Saccomani G., et al., *J. Biol. Chem.* 250, 4802–4809 (1975). The vesicles were lyophilized and kept at −70° C. The protein content was determined by the method of Lowry et al., using bovine serum albumin as standard[see Lowry, O. H., Rosebrough, N. J. and Randall, R. J., *J. Biol. Chem.* 193, 265–275 (1951)].

4-2: Determination of $H^+/K^+$ATPase Activity

Test tubes were divided into 4 groups, each having 3 test tubes. As a control group, group 1 was added with the 10 μl of DMSO. Groups 2, 3 and 4 were administered with the compound prepared in example 34 whose final concentration are 0.17 μM, 0.33 μM and 0.67 μM, respectively. Each group was further divided into 3 small groups, in which enzymes were activated by ATP; ATP and $Mg^{++}$; and ATP, $Mg^{++}$ and $K^+$, respectively.

To all of the test tubes, were added 100 μl of lyophilized vesicles prepared at the concentration of 25 μg protein/ml and then 90 μl of 5 mM Pipes/Tris buffer pH 7.0. The compound prepared in Example 34 was added to each Group until the final concentration thereof became 0.17, 0.33 or 0.67 μM, respectively, They were preincubated for 15 minutes.

50 μl of ATP(3 mM) was added to each of the four Groups and the 50 μl of $MgCl_2$(2 mM) was added only to the 2nd and 3rd small groups of all Groups. Further, to the 3rd small groups of all Groups, were added 50 μl of KCl solution of various concentrations(from 0.1 mM to 30 mM) and then 150μl of Pipes/Tris buffer of pH 7.0. To the rest small groups, Pipes/Tris buffer of pH 7.0 was added until the volume became the same as that of the 3rd small group.

The test tube's were incubated at 37° C. for 30 minutes and then the reaction was terminated by adding 25% cold trichloroacetic acid solution. They were centrifuged by means of a microcentrifuge and the supernatant was taken up for the measurement of the released inorganic phosphate content by an automatic analyzer(CIBA CORNING, Express 550).

In accordance with the same procedures as above, except that 15 and 30 μm of omeprazole and 0.75, 1.5 and 3.0 μm of SK&F96067 were used as comparative substances, released inorganic phosphate content was measured.

The released inorganic phosphate contents of the three small groups were considered as the activity of $H^+/K^+$ ATPase at each of the concentrations employed. The specific activity of $H^+/K^+$ ATPase was calculated from the following equation:

Specific activity$=(A-C)-(B-C)\ldots$ (V)

in which

A is the activity of enzyme activated by ATP, $Mg^{++}$and , $K^+$;

B is the activity of enzyme activated by ATP and $M^{++}$ and

C is the activity of enzyme activated by ATP.

Figure 2:
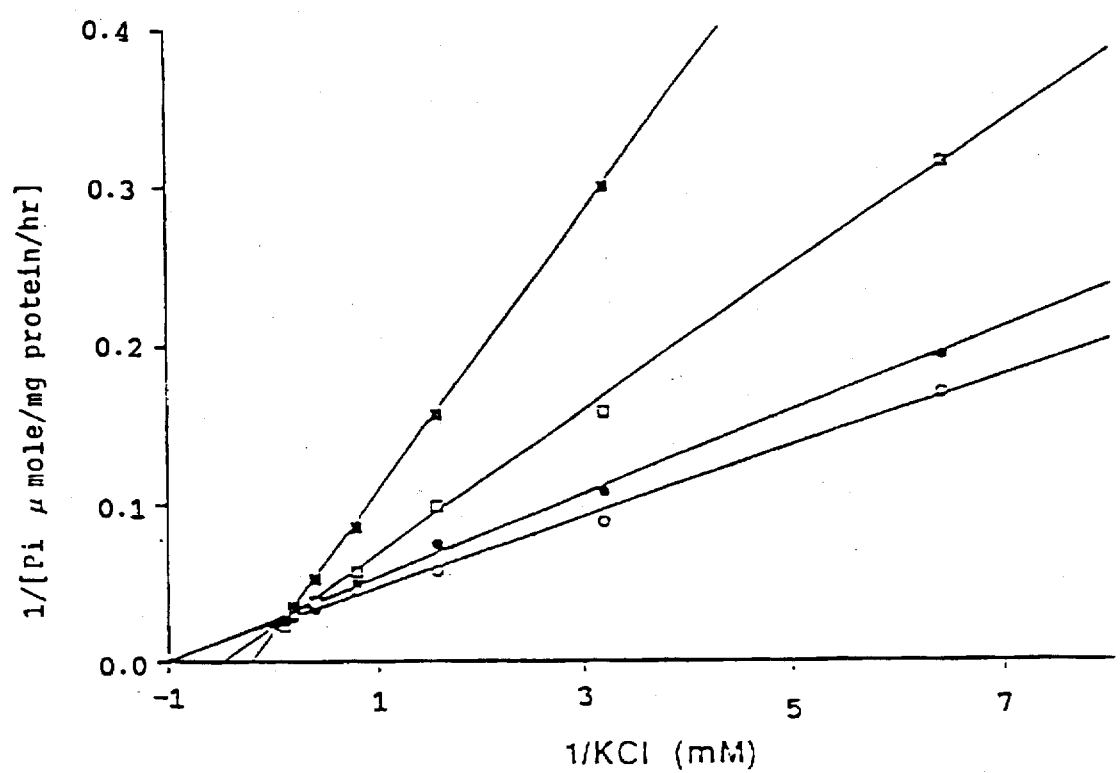
Figure 3:
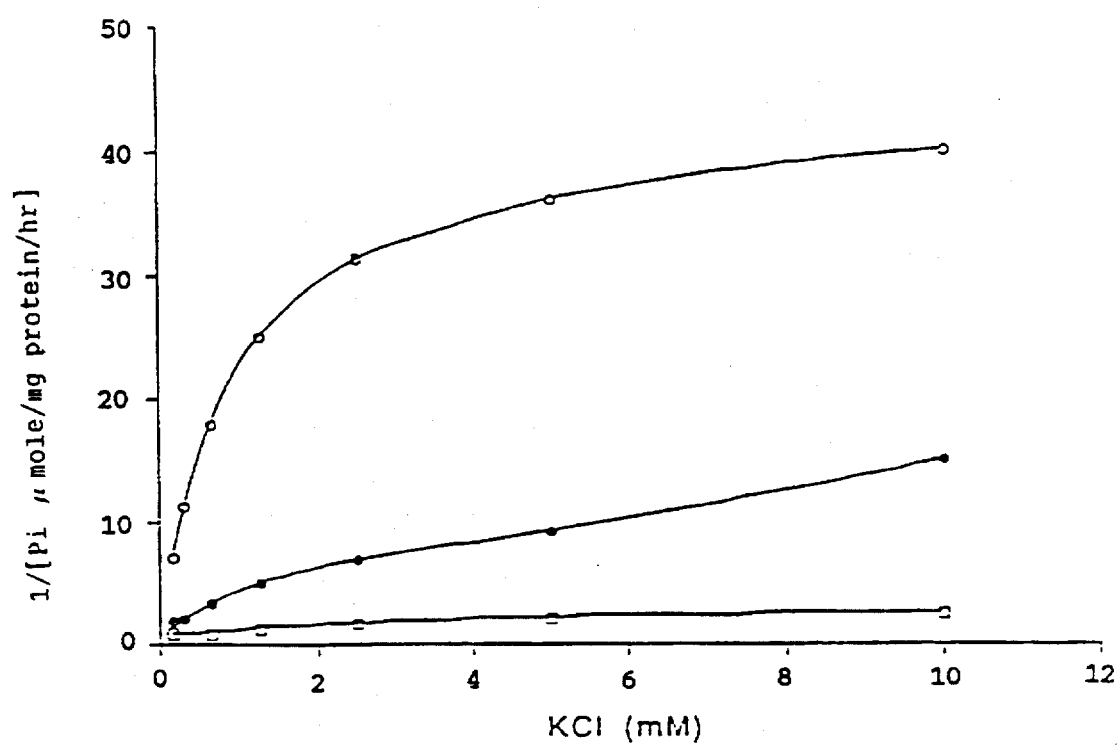

The specific activity, thus calculated, of Groups 1, 2, 3 and 4 which employed DMSO and the compound of Example 34 at 3 different concentrations were then plotted with respect to the concentration of KCl in FIG. 1 according to the method of Lineweaver-Burk, wherein ■, □ and ○ represent the respective concentrations of the compound of Example 34 of 0.67 μM, 0.33 μM and 0.17 μM; and ●represents concentration of the DMSO compound. FIG. 2 depicts the Lineweaver-Burk plot of the specific activities obtained from SK&F96067, wherein ■, □ and ○ represent its respective concentrations of 3.0 μM, 1.5 μM, 0.75 μM; and ●represents concentration of the DMSO compound. FIG. 3 illustrates the Lineweaver-Burk plot of the specific activities obtained from omeprazole, wherein ●and □ represent its concentrations of 15 μM and 30 μM; and ○ represents the concentration of DMSO.

As can be seen from FIGS. 1, 2 and 3, the compound of the present invention and SK&F96067 inhibited competitively with $K^+$ at the $K^+$ binding site of proton pump, whereas omeprazole did not inhibit competitively. Namely, in the case of the compound of the present invention and SK&F96067, $V_{max}$ in the Lineweaver-Burk plot was not changed, whereas $K_m$ value was changed. The Ki values of the present invention compound and SK&F96067 were 0.04 μM and 0.7 μM, respectively. In contrast, in the case of omeprazole, the reaction speed was greatly reduced in comparison with the control values at the concentrations of 15 and 30 μM; and the inhibition of the enzyme activity was not overcome by increasing the concentration of KCl. In view of this, it was confirmed that omeprazole was not competitive inhibition relationship with $K^+$.

4-3: Reversibility of Inhibition

The inhibition mechanism of proton pump activity by the present invention compound was tested in accordance with the so-called Dilution and Washout method [see D. J. Keeling, et al., Biochemical Pharmacology 42(1) 123-130 (1991)].

Namely, test tubes were divided into two group, groups 1 and 2 to be administered with DMSO and the compound prepared in Example 34, respectively. 10 μl of each of DMSO and the compound(6 μM) prepared in Example 34 was added to groups 1 and 2, respectively.

To all two groups, was added 100 μl of lyophilized vesicles prepared in Experiment 4-1 at the concentration of 100 μg protein 1 ml. Then, 5 mM Pipes/Tris buffer(pH 6.4) was added to the three groups until the volume of test tubes became 150 μl. After the preincubation for 15 minutes, $H^+/K^+$ ATPase activity was measured in accordance with the same procedures as in Experiment 4-2. The concentrations of the test substances as indicated above are the final concentrations.

After the completion of preincubation, each group was diluted 50 times with 5 mM Pipes/Tris buffer(pH 6.4), and then centrifuged for 60 minutes by means of Beckman ultracentrifuge(Model L8-80). The supernatant was discarded and the pellet was suspended with 5 mM Pipes/Tris buffer pH 6.4 until the volume became the same as the preincubation volume. Thereafter, the inhibition of $(H^++K^+)$-ATPase activity was measured in accordance with the same procedures as in Experiment 4-2; and it was further measured in accordance with the same procedures as above, except the 60 μM omeprazole and 60 μM SK&F96067 were used as comparative substances. The inhibition of $H^+/K^+$ ATPase activity before and after the Dilution and Washout procedures is shown in Table 4.

TABLE 4

| The inhibition of $H^+/K^+$ ATPase activity | | |
|---|---|---|
| | Before Dilution and Washout | After Dilution and Washout |
| Compound of Example 34 | 84(%) | 16(%) |
| Omeprazole | 80(%) | 67(%) |
| SK&F96067 | 80(%) | 0(%) |

As can be seen from Table 4, omeprazole inhibited 80% of the enzyme activity before the Dilution and Washout procedure and 67% of the activity even after the Dilution and Washout procedure. This shows that omeprazole did not leave the binding sites of the enzyme after the Dilution and Washout procedure, indicating that the inhibition by omeprazole is irreversible.

In contrast, SK&F96067 and the present invention compound inhibited 80% and 84%, respectively, of the enzyme activity before the Dilution and Washout procedure, whereas they showed no or 16% of inhibition of the enzyme activity after the Dilution and Washout procedure. This indicates that the inhibition of the enzyme activity of SK&F96067 and the present invention compound is reversible.

While the invention has been described with respect to the above specific embodiments only, other modifications and variations may be made without departing from the spirit and scope of the present invention as set forth in the following claims.

What is claimed is:

1. A quinazoline derivative represented by formula(I) and a pharmaceutically acceptable salt thereof:

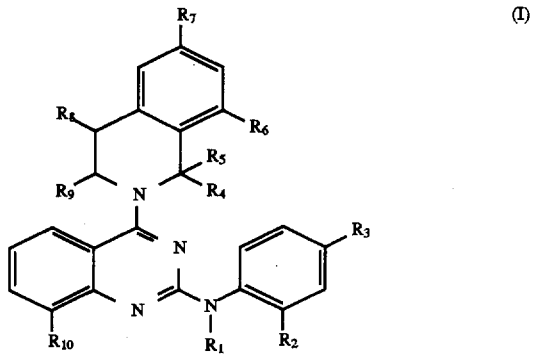

wherein $R_1$ and $R_2$ are each hydrogen or a $C_1$-$C_4$ alkyl group;

$R_3$ is hydrogen or a halogen;

$R_4$, $R_5$, $R_6$, $R_7$, $R_8$ and $R_9$, which may be the same or different, are each hydrogen, a $C_1$-$C_4$ alkyl group, a cyclopropyl group, or a $C_1$-$C_4$ alkyl group substituted with a halogen; and $R_{10}$ is a methoxy group.

2. The quinazoline derivative of claim 1, which is selected from the group consisting 8-methoxy-2-(phenylamino)-4-(1,2,3,4-tetrahydroisoquinolin-2-yl)quinazoline;

8-methoxy- (N-methylphenylamino-4-(1,2,3,4-tetrahydroisoquinolin-2-yl)quinazoline;

8-methoxy-2-(4-fluorophenylamino)-4-(1,2,3,4-tetrahydroisoquinolin-2-yl) quinazoline;

8-methoxy-2-(4-fluoro-2-methylphenylamino) -4-(1,2,3,4-tetrahydroisoquinolin-2-yl) quinazoline;

8-methoxy-2-(4-fluoro-N-methylphenylamino)-4-(1,2,3,4-tetrahydroisoquinolin-2-yl) quinazoline;

8-methoxy-2-(4-fluorophenylamino)-4-(1-methyl-1,2,3,4-tetrahydroisoquinolin-2-yl ) quinazoline;

8-methoxy-2-(4-fluoro-2-methylphenylamino)-4-(1-methyl-1,2,3,4-tetrahydroisoquinolin-2-yl) quinazoline;

(R)-8-methoxy-2-(4-fluoro-2-methylphenylamino)-4-(1-methyl-1,2,3,4-tetrahydroisoquinolin-2-yl) quinazoline;

(S) -8-methoxy-2-(4-fluoro-2-methylphenylamino)-4-(1-methyl-1,2,3,4- tetrahydroisoquinolin-2-yl) quinazoline;

8-methoxy-2-(N-methylphenylamino)-4-(1-methyl-1,2,3,4-tetrahydroisoquinolin-2-yl) quinazoline;

8-methoxy-2-(4-fluoro-N-methylphenylamino)-4-(1-methyl-1,2,3,4-tetrahydroisoquinolin-2-yl) quinazoline;

2-(4-fluoro-2-methylphenylamino) -8-methoxy-4-(1-trifluoromethyl-1,2,3,4-tetrahydroisoquinolin-2-yl) quinazoline;

2-(4-fluorophenylamino)-8-methoxy-4-(1-fluoromethyl-1,2,3,4-tetrahydroisoquinolin-2-yl)quinazoline;

2-(4-fluoro-2-methylphenylamino)-8-methoxy-4-(1-fluoro-methyl-1,2,3,4-tetrahydroisoquinolin-2-yl)quinazoline;

8-methoxy-2-(4-fluorophenylamino)-4-(1-ethyl-1,2,3,4-tetrahydroisoquinolin-2-yl)quinazoline;

8-methoxy-2-(2-methyl-4-fluorophenylamino)-4-(1-ethyl-1,2,3,4-tetrahydroisoquinolin-2-yl)quinazoline;

2-(4-fluoro-2-methylphenylamino)-8-methoxy-4-(1-cyclopropyl-1,2,3,4-tetrahydroisoquinolin-2-yl)quinazoline;

2-(4-fluorophenylamino)-8-methoxy-4-(3-methyl-1,2,3,4-tetrahydroisoquinolin-2-yl)quinazoline;

2-(4-fluoro-2-methylphenylamino)-8-methoxy-4-(3-methyl-1,2,3,4-tetrahydroisoquinolin-2-yl)quinazoline;

2-(4-fluorophenylamino)-8-methoxy-4-(1,1-dimethyl-1,2,3,4-tetrahydroisoquinolin-2-yl)quinazoline;

2-(4-fluoro-2-methylphenylamino)-8-methoxy-4-(1,1-dimethyl-1,2,3,4-tetrahydroisoquinolin-2-yl)quinazoline;

2-(4-fluorophenylamino)-8-methoxy-4-(1,8-dimethyl-1,2,3,4-tetrahydroisoquinolin-2-yl)quinazoline;

2-(4-fluoro-2-methylphenylamino)-8-methoxy-4-(1,8-dimethyl-1,2,3,4-tetrahydroisoquinolin-2-yl)quinazoline;

2-(4-fluorophenylamino)-8-methoxy-4-(1,6-dimethyl-1,2,3,4-tetrahydroisoquinolin-2-yl)quinazoline;

2-(4-fluoro-2-methylphenylamino)-8-methoxy-4-(1,6-dimethyl-1,2,3,4-tetrahydroisoquinolin-2-yl)quinazoline;

2-(4-fluorophenylamino)-8-methoxy-4-(1,4-dimethyl-1,2,3,4-tetrahydroisoquinolin-2-yl)quinazoline;

2-(4-fluoro-2-methylphenylamino)-8-methoxy-4-(1,4-dimethyl-1,2,3,4-tetrahydroisoquinolin-2-yl)quinazoline;

8-methoxy-2-(4-fluorophenylamino)-4-(1,8-ethano-1,2,3,4-tetrahydroisoquinolin-2-yl)quinazoline;

8-methoxy-2-(4-fluoro-2-methylphenylamino)-4-(1,8-ethano-1,2,3,4-tetrahydroisoquinolin-2-yl)quinazoline;

2-(4-fluoro-2-methylphenylamino)-8-methoxy-4-(1-methyl-1,2,3,4-tetrahydroisoquinolin-2-yl)quinazoline; and a pharmaceutically acceptable salt thereof.

3. The pharmaceutically acceptable salt of the quinazoline derivative of claim 1, which is selected from the group consisting of hydrochloride, sulfate, phosphate, nitrate, tartrate, fumarate, citrate, mesylate and acetate salts.

4. A process for preparing quinazoline derivatives of formula(I) defined in claim 1, which comprises reacting a compound of formula(II) with a compound of formula(III) to give a compound of formula(IV), which is then reacted with a compound of formula(V):

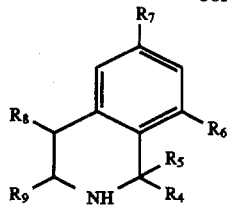 (II)

-continued

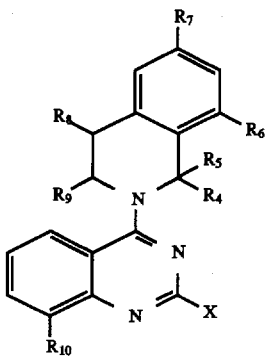 (III)

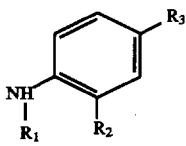 (IV)

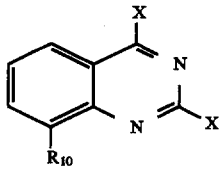 (V)

wherein $R_1$, $R_2$, $R_3$, $R_4$, $R_5$, $R_6$, $R_7$, $R_8$, $R_9$ and $R_{10}$ have the same meanings as defined in claim 1, and X is chlorine.

5. The process of claim 4, where the reaction of the compound of formula(II) with the compound of formula(III) is carried out in a solvent selected from the group consisting of dichloromethane, acetone, acetonitrile, tetrahydrofuran and a mixture thereof with water, and a base selected from the group consisting of triethylamine, N,N-dimethylaniline and pyridine.

6. A 2-chloro-4-(1-substituted-1,2,3,4-tetrahydroisoquinolin-2-yl)quinazoline of formula(IV):

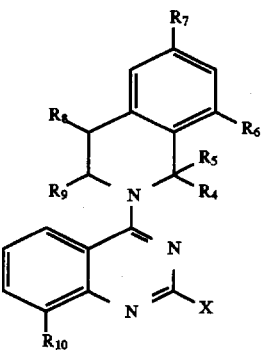 (IV)

wherein $R_4$, $R_5$, $R_6$, $R_7$, $R_8$, $R_9$, and $R_{10}$ have the same meanings as defined in claim 1, and X is chlorine.

7. A process for preparing a compound of formula (IV), which comprises reacting a compound of formula(II) and a compound of formula(III):

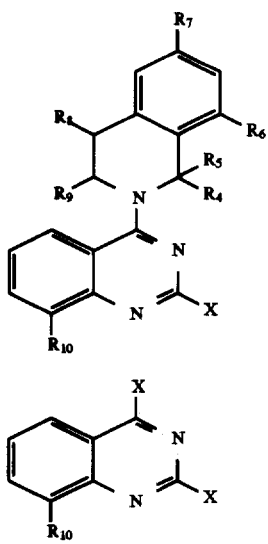

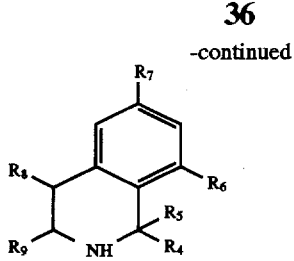

wherein $R_4$, $R_5$, $R_6$, $R_7$, $R_8$, $R_9$ and $R_{10}$ have the same meanings as defined in claim 1, and X is chlorine.

8. The process of claim 7, where the reaction is carried out in a solvent selected from the group consisting of dimethylformamide, p-dioxane and dimethyl-sulfoxide.

9. A pharmaceutical composition for treating peptic ulcer, which comprises a therapeutically effective amount of the quinazoline derivative or pharmaceutically acceptable salt thereof recited in claim 1 and a pharmaceutically acceptable carrier.

* * * * *